(12) United States Patent
Tarumoto et al.

(10) Patent No.: US 12,245,745 B2
(45) Date of Patent: *Mar. 11, 2025

(54) ELEVATOR ATTACHMENT AND ENDOSCOPE

(71) Applicant: HOYA CORPORATION, Tokyo (JP)

(72) Inventors: Tetsuya Tarumoto, Tokyo (JP); Takahiro Hatoma, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 626 days.

This patent is subject to a terminal disclaimer.

(21) Appl. No.: 17/616,787

(22) PCT Filed: Jun. 4, 2020

(86) PCT No.: PCT/JP2020/022052
§ 371 (c)(1),
(2) Date: Dec. 6, 2021

(87) PCT Pub. No.: WO2020/246532
PCT Pub. Date: Dec. 10, 2020

(65) Prior Publication Data
US 2022/0304556 A1    Sep. 29, 2022

(30) Foreign Application Priority Data

Jun. 7, 2019 (JP) .................................. 2019-106998

(51) Int. Cl.
*A61B 1/00*     (2006.01)
*A61B 1/012*    (2006.01)

(52) U.S. Cl.
CPC ...... *A61B 1/00098* (2013.01); *A61B 1/00101* (2013.01); *A61B 1/012* (2013.01); *A61B 1/00177* (2013.01)

(58) Field of Classification Search
CPC ............ A61B 1/00098; A61B 1/00101; A61B 1/00177; A61B 1/012; A61B 1/0125; A61B 1/018
See application file for complete search history.

(56) References Cited

U.S. PATENT DOCUMENTS 5,562,600 A * 10/1996 Matsuno ............ A61B 1/00098
600/107
5,569,157 A * 10/1996 Nakazawa ......... A61B 1/00098
600/106

(Continued)

FOREIGN PATENT DOCUMENTS

JP         9-122067        5/1997
JP         2013-183964     9/2013

(Continued)

OTHER PUBLICATIONS

International Search Report issued in International Patent Application No. PCT/JP2020/022052, dated Aug. 11, 2020, along with an English translation thereof.

(Continued)

*Primary Examiner* — Aaron B Fairchild
(74) *Attorney, Agent, or Firm* — Greenblum & Bernstein, P.L.C.

(57) ABSTRACT

An elevator attachment attachable to and detachable from an endoscope including an inclined surface inclined relative to a longitudinal direction of an insertion part, an elevator recess having a first inner wall and a second inner wall that faces the first inner wall and being opened toward the inclined surface and a lever pivotally provided inside the elevator recess, and the elevator attachment comprises a holding body including an inclined surface plate covering a part of the inclined surface, a first plate raising from an edge of the inclined surface plate and located along the first inner wall and a second plate abutting against the second inner (Continued)

wall, and an elevator pivotally supported between the first plate and the second plate and including a lever connection part to be connected to the lever.

12 Claims, 42 Drawing Sheets

(56) References Cited

U.S. PATENT DOCUMENTS

| | | |
|---|---|---|
| 2016/0206180 A1 | 7/2016 | Hosogoe |
| 2016/0270636 A1 | 9/2016 | Iwasaka et al. |
| 2017/0112363 A1 | 4/2017 | Morimoto |
| 2018/0206708 A1* | 7/2018 | Miller ................ A61B 1/00098 |
| 2018/0249894 A1* | 9/2018 | Kolberg ............. A61B 1/00098 |
| 2019/0015172 A1* | 1/2019 | Yamaya ............. A61B 1/00098 |
| 2019/0117045 A1 | 4/2019 | Hosogoe |
| 2019/0231173 A1 | 8/2019 | Hosogoe |

FOREIGN PATENT DOCUMENTS

| | | |
|---|---|---|
| JP | 2016-131578 | 7/2016 |
| JP | 2018-118080 | 8/2018 |
| WO | 2018/070515 | 4/2018 |

OTHER PUBLICATIONS

Extended European Search Report Issued in Corresponding EP Patent Application No. 20818350.9, dated Jan. 10, 2023.

* cited by examiner

F I G. 2 9
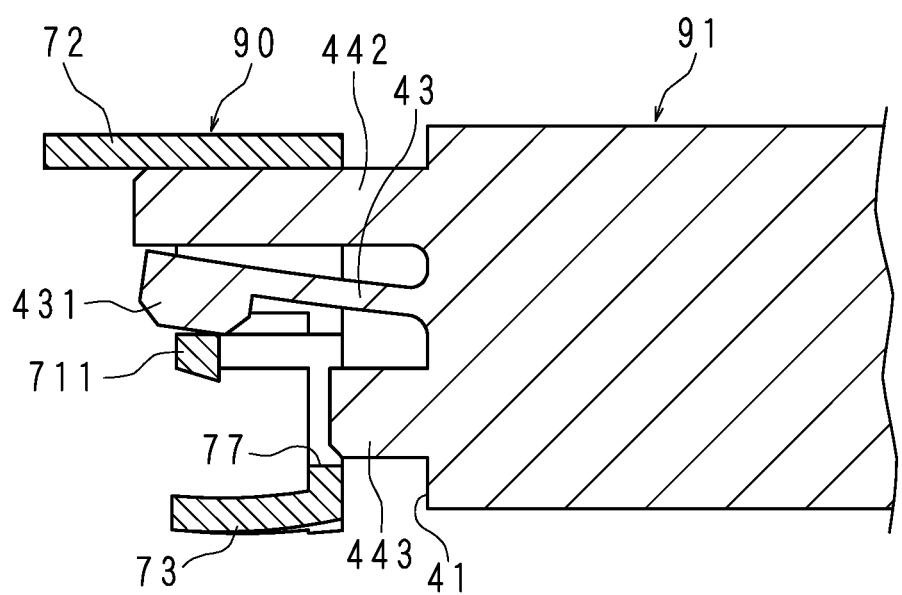

F I G. 4 1
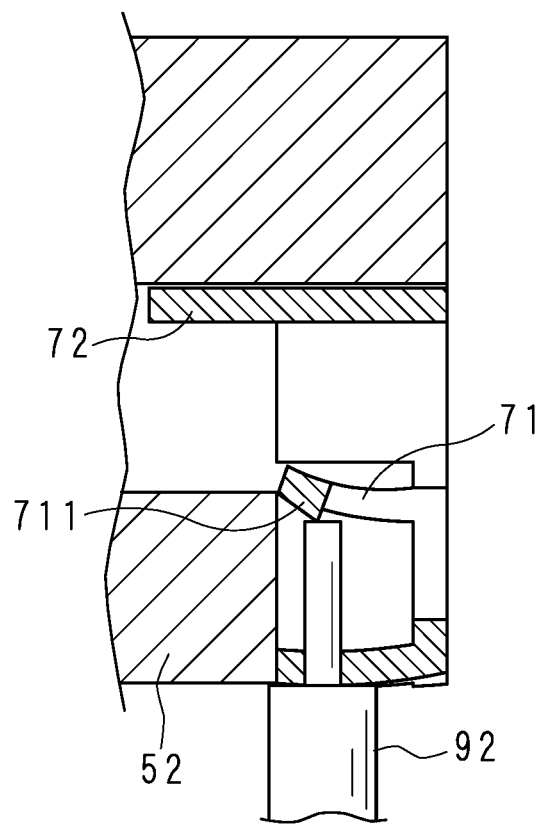

ELEVATOR ATTACHMENT AND ENDOSCOPE

CROSS-REFERENCE TO RELATED APPLICATIONS

This application is the national phase under 35 U. S. C. § 371 of International Patent Application PCT/JP2020/022052 which has an International filing date of Jun. 4, 2020, which claims priority under 35 U.S.C. § 119 on Patent Application No. 2019-106998 filed in Japan on Jun. 7, 2019, and designated the United States of America.

FIELD

The present invention relates to an elevator attachment and an endoscope.

BACKGROUND

In Japanese Patent Application Laid-Open No. 2018-118080, an endoscope cap with an elevator and an endoscope used in combination with the endoscope cap have been proposed. After completion of endoscopy, the elevator is detached together with the endoscope cap to allow easy cleaning of the endoscope.

SUMMARY

However, there are some endoscopes having a structure making it difficult to use the endoscope cap described the said patent application, such as a so-called forward oblique view type endoscope having a viewing direction for optical observation forward obliquely to an insertion part.

According to an aspect, an object is to provide an elevator attachment or the like that enables an easy cleaning of an endoscope by removing the elevator attachment after endoscopy.

In an elevator attachment attachable to and detachable from an endoscope, the endoscope includes an inclined surface inclined relative to a longitudinal direction of an insertion part, an elevator recess having a first inner wall and a second inner wall that faces the first inner wall and being opened toward the inclined surface, and a lever pivotally provided inside the elevator recess, and the elevator attachment comprises a holding body including an inclined surface plate covering a part of the inclined surface, a first plate extending from an edge of the inclined surface plate and located along the first inner wall and a second plate abutting against the second inner wall, and an elevator pivotally supported between the first plate and the second plate and including a lever connection part to be connected to the lever.

Effects of Invention

According to an aspect, an elevator attachment or the like can be provided that enables easy cleaning of an endoscope by being removed after endoscopy.

The above and further objects and features will more fully be apparent from the following detailed description with accompanying drawings.

BRIEF DESCRIPTION OF THE DRAWINGS

FIG. 29 illustrates a method of attaching the elevator attachment to the first jig.

FIG. 41 illustrates a method of removing an elevator attachment according to Embodiment 2 from the endoscope.

EMBODIMENT 1

Figure 1:
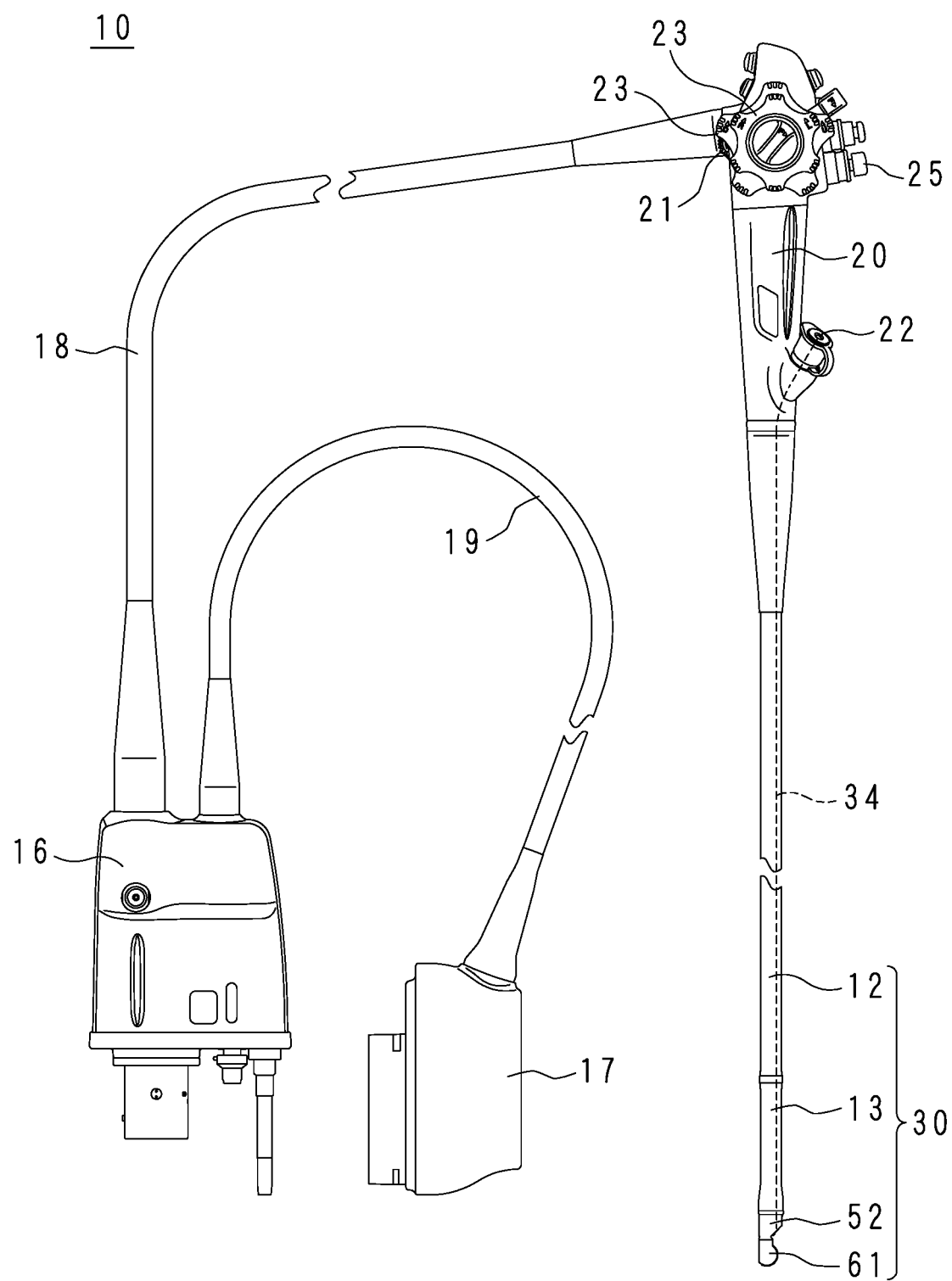
FIG. 1 illustrates an outer appearance of an endoscope.

FIG. 1 illustrates an outer appearance of an endoscope 10. The endoscope 10 according to the present embodiment is an ultrasound endoscope provided with a convex-shaped ultrasound probe 61 at the distal end.

The endoscope 10 has an operation part 20 and an insertion part 30. The operation part 20 has an elevator operation lever 21, a channel inlet 22, a water supply button 25 and two bending knobs 23. The operation part 20 is connected to a video processor, a light source device, a display device and so forth that are not illustrated via a first tube 18 and a first connector 16. The operation part 20 is also connected to an ultrasound processor that is not illustrated via a second tube 19 extending form the first connector 16 and a second connector 17.

The insertion part 30 has a long flexible section 12 having one end connected to the operation part 20. The ultrasound probe 61 is connected to the other end of the flexible section 12 via a bending section 13 and a distal end frame 52. The bending section 13 is connected to the bending knobs 23 via a bending wire inserted through the flexible section 12 and is bent in response to the operation of the bending knobs 23.

The channel inlet 22 and the distal end frame 52 are connected with each other by a tubular channel 34. The distal end frame 52 contains an illumination optical system, an observation optical system and so forth to be used when observation using an optical image is performed. The detailed structure of the distal end frame 52 will be described later.

The endoscope 10 is used when the insertion part 30 is inserted from the mouth of a subject to the gastrointestinal tract to perform observation by an optical image and observation by ultrasound and to perform various treatments. In the following description, the longitudinal direction of the insertion part 30 will be referred to as an insertion direction. Likewise, along the insertion direction, the side closer to the operation part 20 will be referred to as an operation part side, whereas the side farther from the operation part 20 will be referred to as a distal side.

Figure 2:
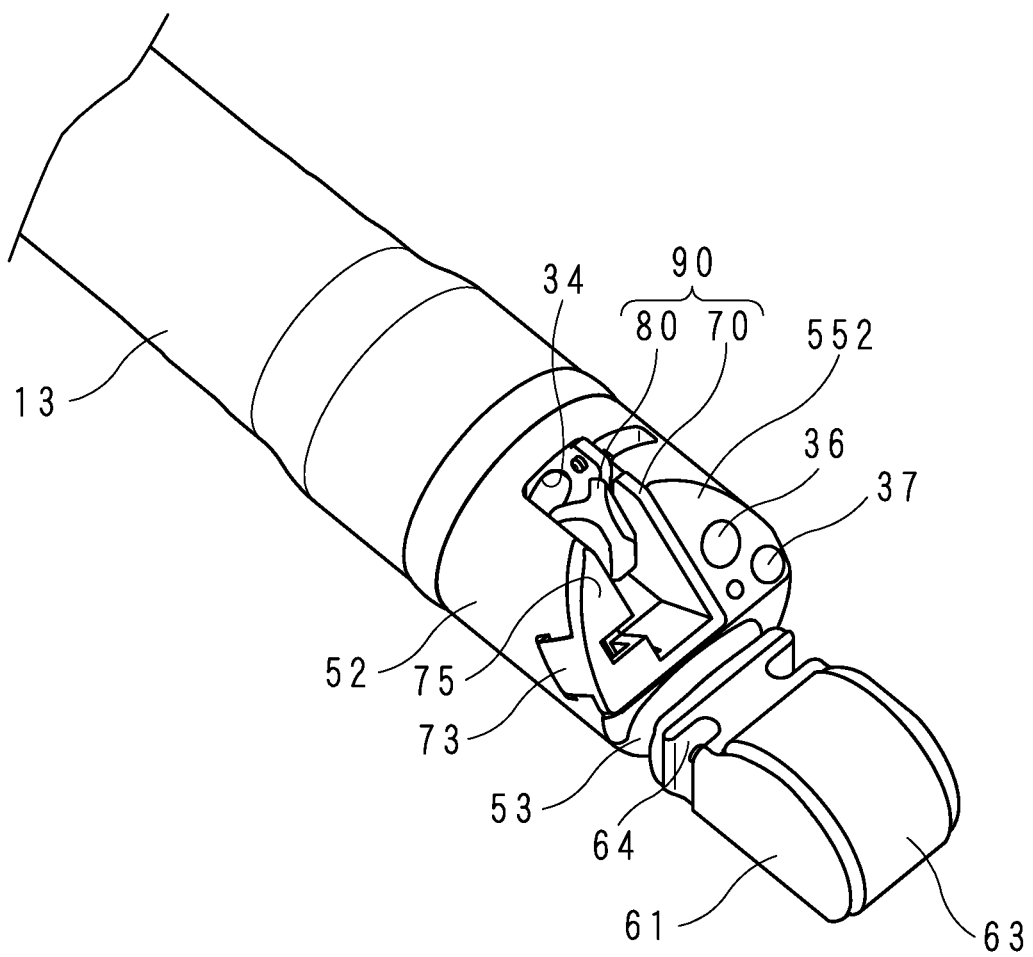
FIG. 2 is a perspective view illustrating a distal end of an insertion part to which an elevator attachment is attached.

FIG. 2 is a perspective view illustrating a distal end of the insertion part 30 to which an elevator attachment 90 is attached. The structure of the elevator attachment 90 will be described later. The ultrasound probe 61 is a so-called convex type having a convex-shaped ultrasound wave transmitting and receiving surface 63.

The ultrasound probe 61 has two balloon water supply and drain grooves 64 that are disposed in a direction perpendicular to the insertion direction at the positions more toward the operation part side than the ultrasound wave transmitting and receiving surface 63.

The distal end frame 52 is substantially cylindrical and has a second inclined surface 552 inclined relative to the axial direction at the distal end side. The ultrasound wave transmitting and receiving surface 63 and the second inclined surface 552 are disposed on the same side relative to the insertion direction. An observation window 36 and an illumination window 37 are disposed on the second inclined surface 552. The endoscope 10 is a so-called forward oblique view type endoscope that performs observation by illuminating the portion obliquely forward relative to the insertion direction. The distal frame 52 is provided with a balloon fixing groove 53 around its periphery on its distal end side.

Figure 3:
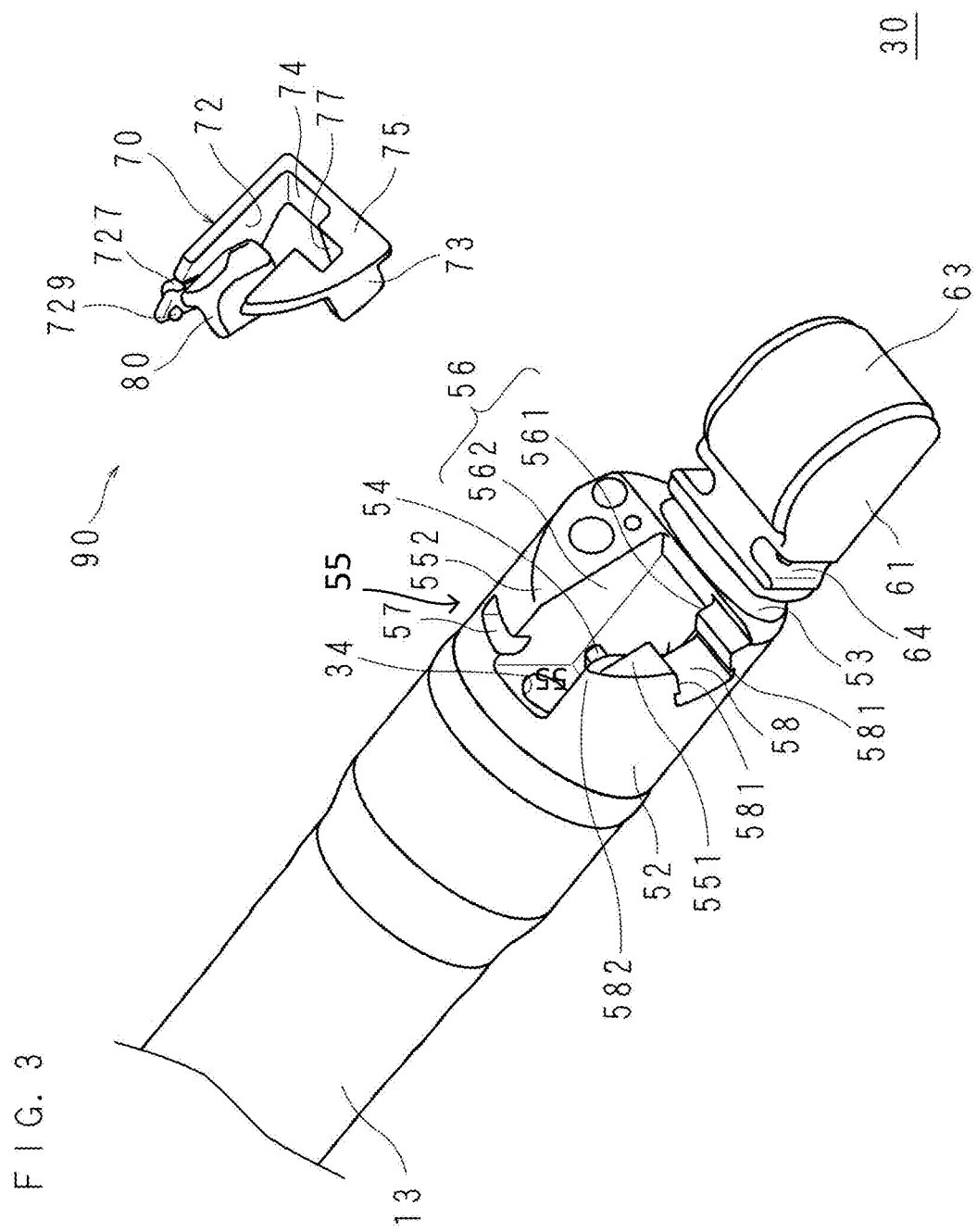
FIG. 3 is a perspective view illustrating the elevator attachment and the distal end of the insertion part from which the elevator attachment is detached.

FIG. 3 is a perspective view illustrating the elevator attachment 90 and the distal end of the insertion part 30 from which the elevator attachment 90 is detached.

The distal frame 52 is separated to both sides by an elevator recess 56 being a substantially U-shaped concave extending from the distal end side to the operation part side. The elevator recess 56 has a channel 34 opened at its end on the operation part side. The elevator recess 56 has a second inner wall 562 continuous to the second inclined surface 552 and a first inner wall 561 opposed to the second inner wall 562. A first inclined surface 551 is continuous to the first inner wall 561.

The first inclined surface 551 is substantially parallel to the second inclined surface 552 and is located more toward the operation part side than the second inclined surface 552. In the following description, the first inclined surface 551 and the second inclined surface 552 may collectively be referred to as an inclined surface 55 in the following description. The elevator recess 56 is opened toward the inclined surface 55.

Figure 4:
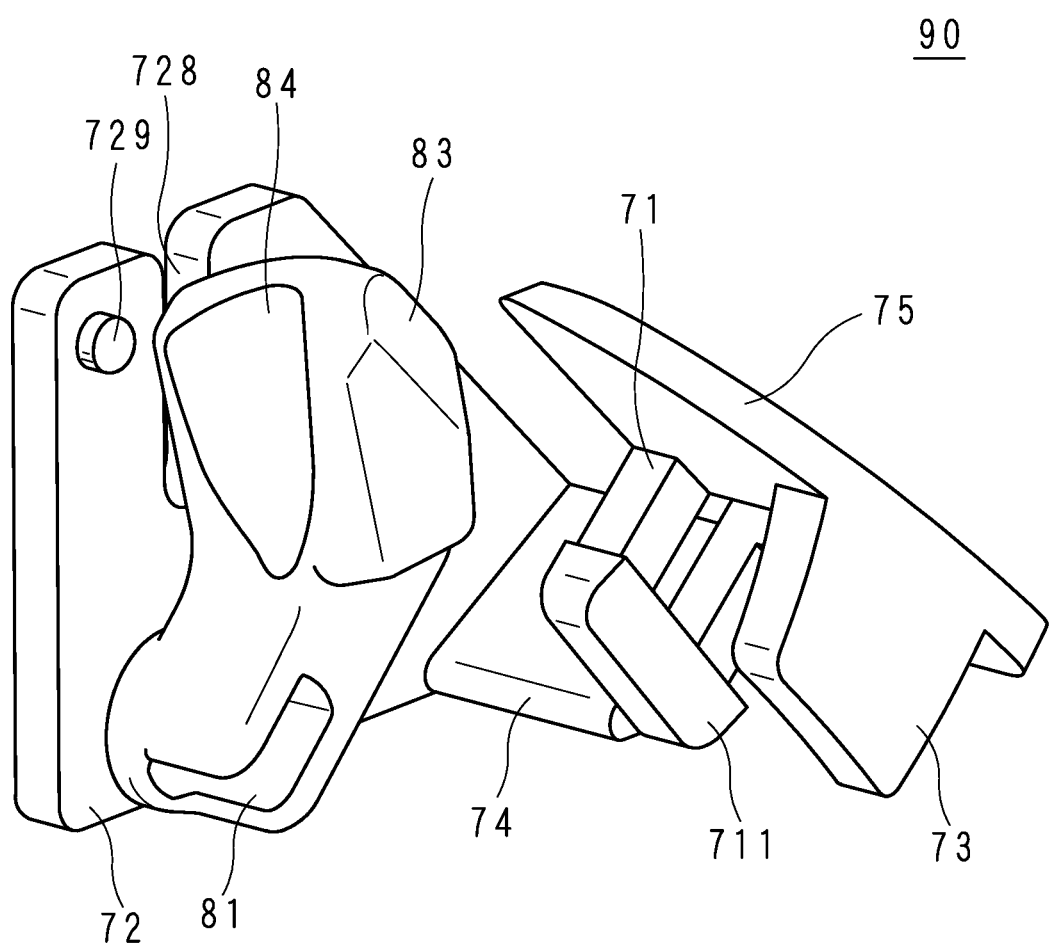
FIG. 4 is a perspective view of the elevator attachment.

FIG. 4 is a perspective view of the elevator attachment 90. FIG. 4 shows the elevator attachment 90 when viewed from a direction different from FIG. 3. The configuration of the elevator attachment 90 will now be summarized with reference to FIG. 3 and FIG. 4.

The elevator attachment 90 includes a holding body 70 and an elevator 80. The holding body 70 includes a substantially triangular inclined surface plate 75 as well as a first plate 71, a second plate 72 and a third plate 73. The first plate 71 and the third plate 73 extend from two sides of the inclined surface plate 75 on the same side so as to be substantially perpendicular to the sides. The second plate 72 and the first plate 71 are substantially parallel to each other. The inclined surface plate 75 and the second plate 72 are connected via a connection part 74.

The first plate 71 is provided with an engaging hook 711 extending in three directions except for the second plate 72 side. The inclined surface plate 75 is provided with a substantially U-shaped cutaway portion 77 extending from the second plate 72 side to the third plate 73 side. The cutaway portion 77 also halves the first plate 71.

The second plate 72 is substantially pentagonal. A first side 721 (see FIG. 15) of the second plate 72 is connected to the connection part 74. A second side 722 (see FIG. 15) adjacent to the first side 721 is substantially parallel to the inclined surface plate 75. A division slot 728 having substantially the same thickness as the second plate 72 is disposed so as to extend substantially perpendicular to a third side 723 (see FIG. 15) adjacent to the second side 722. On the surface of the second plate 72 facing the first plate 71, a stopper protrusion 729 is provided. The stopper protrusion 729 is disposed between a fourth side 724 (see FIG. 15) adjacent to the third side 723 and the division slot 728. On the surface opposite to the surface provided with the stopper protrusion 729, an engagement protrusion 727 is provided so as to face the division slot 728.

The first side 721 is substantially perpendicular to the second side 722 while the third side 723 is substantially perpendicular to the fourth side 724. Likely, the fourth side 724 is substantially perpendicular to a fifth side 725 (see FIG. 15) adjacent to the fourth side 724. The elevator 80 is pivotally supported near the angle formed by the fourth side 724 and the fifth side 725 of the second plate 72. The details of the structure of a part for supporting the elevator 80 will be described later.

The elevator 80 has an elevating part 83 with a spoon-shaped recess 84 on one surface. A lever connection part 81 being a groove opened in two directions is provided at the end away from the recess 84 of the elevating part 83. The details of the structure of the elevator 80 will be described later.

The third plate 73 is gently curved and, if the elevator attachment 90 is attached to the distal end frame 52 as shown in FIG. 2, is gradually continuous to the surface of the distal end frame 52. The surface of the inclined surface plate 75 is on substantially the same level of the second inclined surface 552. In other words, the first inclined surface 551 is located more toward the operation part side than the second inclined surface 552 by the thickness of the inclined surface plate 75.

Figure 5:
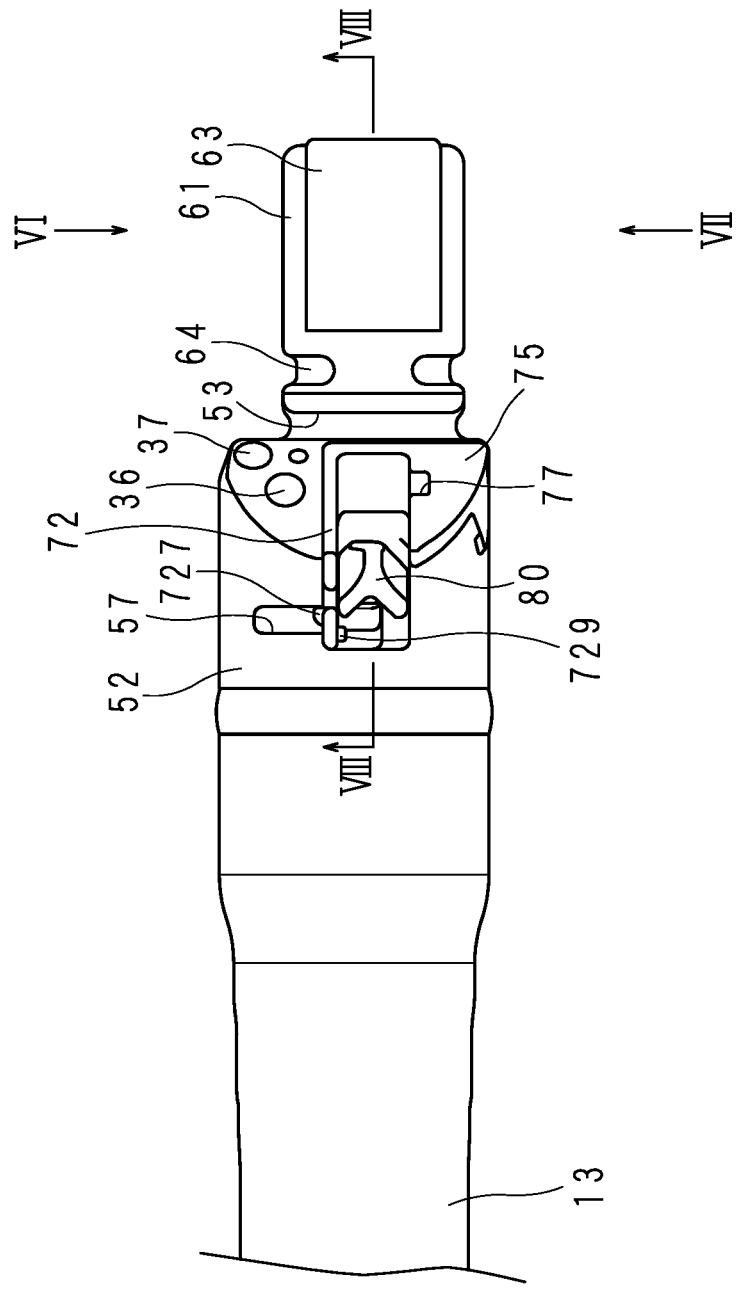
FIG. 5 is a front view of the insertion part to which the elevator attachment is attached.
Figure 6:
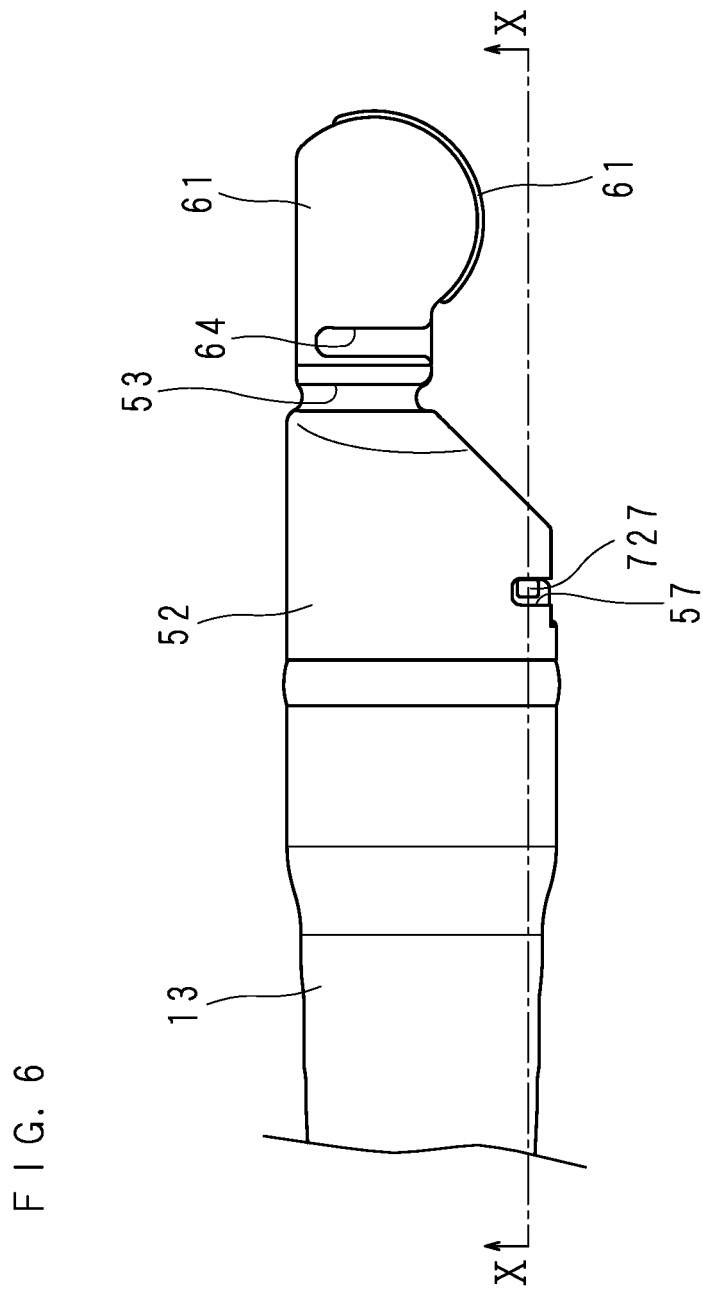
FIG. 6 is a figure viewing the insertion part from the arrow direction VI in FIG. 5.
Figure 7:
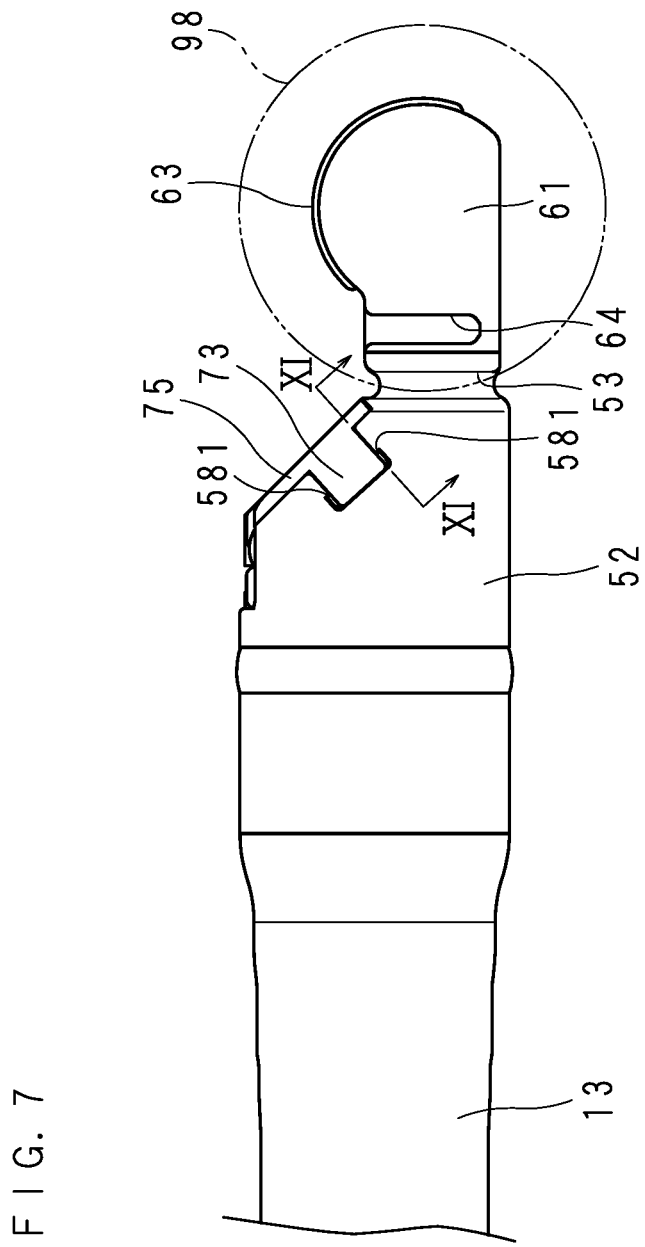
FIG. 7 is a figure viewing the insertion part from the arrow direction VII in FIG. 5.
Figure 8:
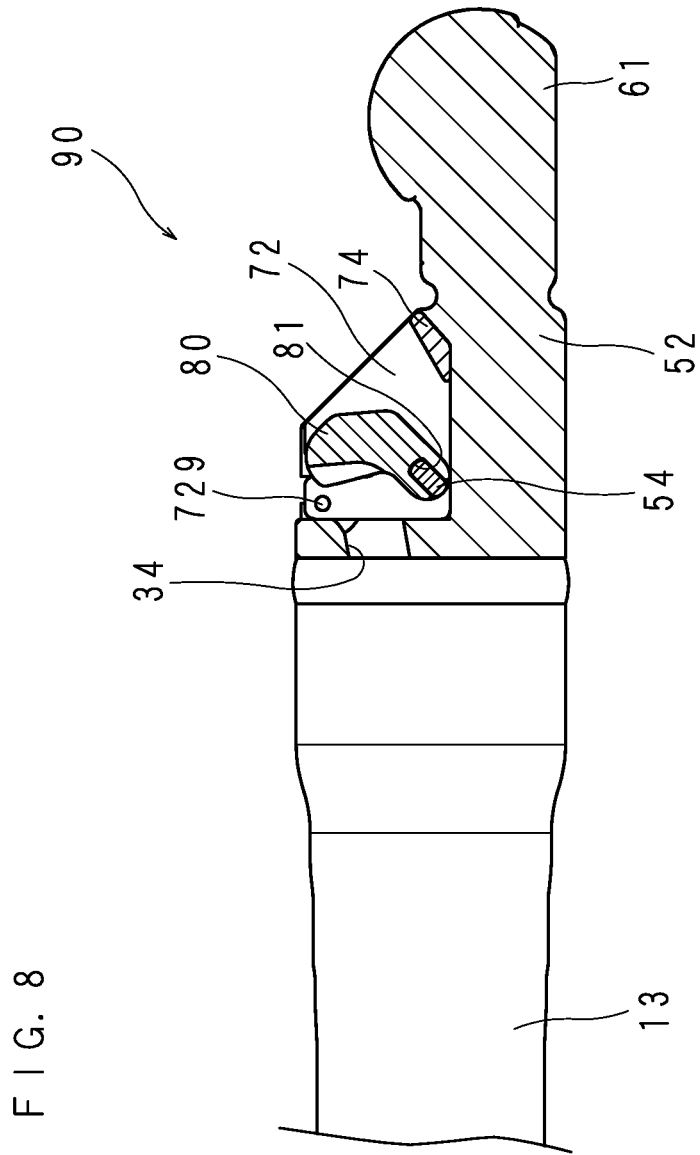
FIG. 8 is a partially sectional view of the insertion part taken along the line VIII-VIII in FIG. 5.
Figure 9:
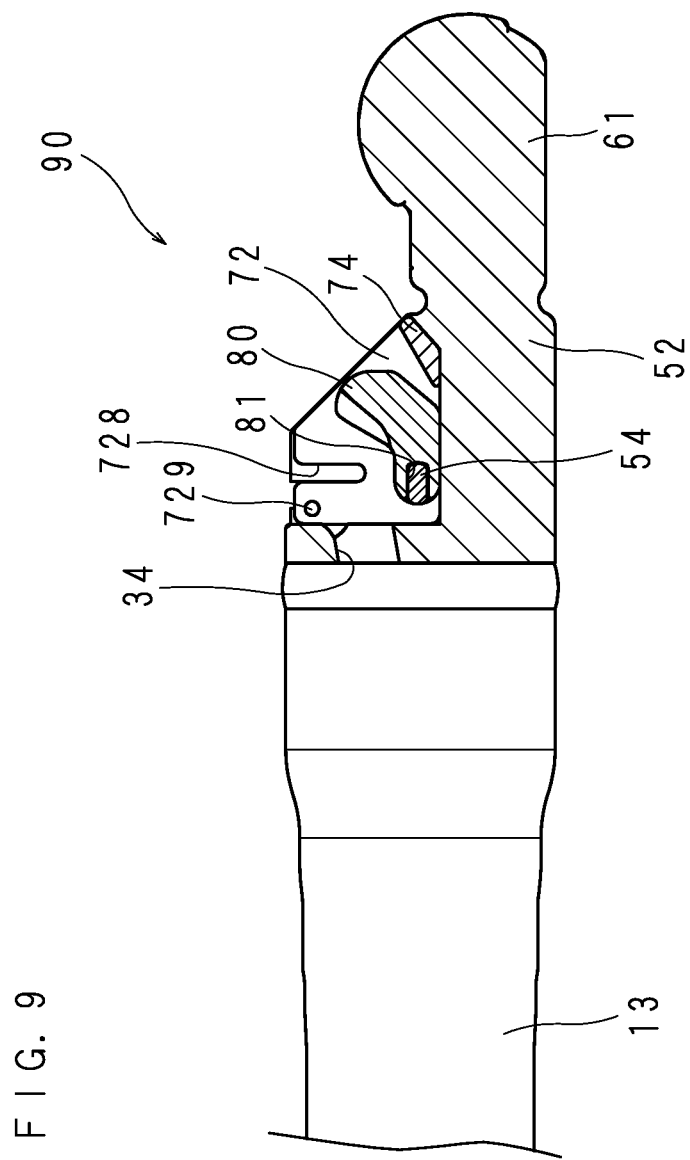
FIG. 9 illustrates the operation of an elevator.
Figure 10:
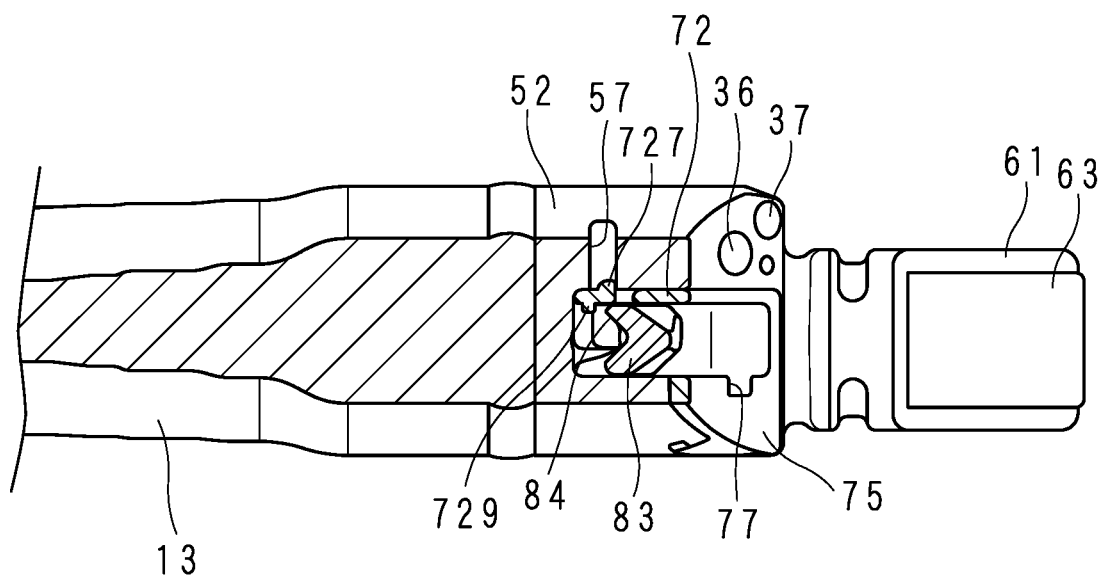
FIG. 10 is a partially sectional view of the insertion part taken along the line X-X in FIG. 6.
Figure 11:
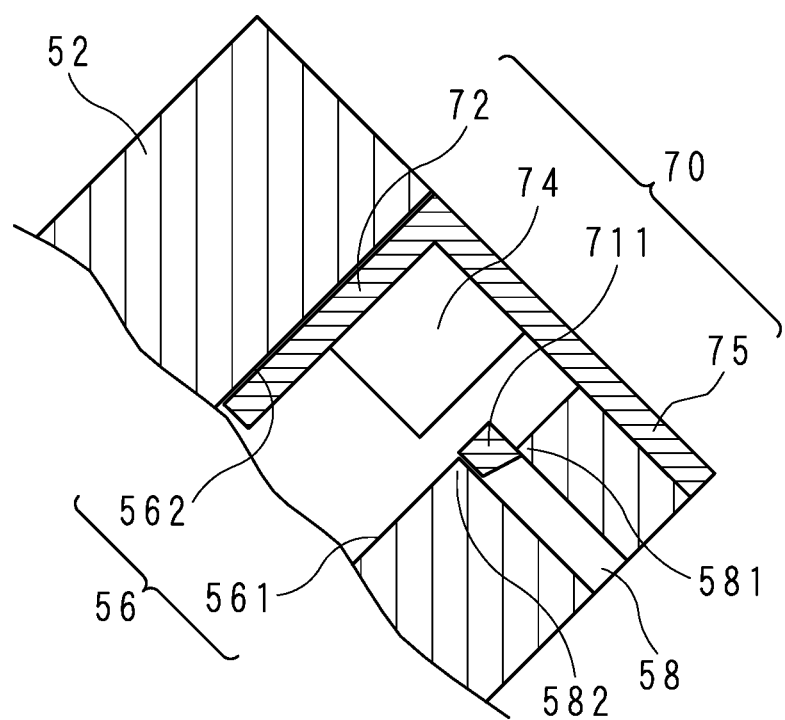
FIG. 11 is a partially sectional view of the insertion part taken along the line XI-XI in FIG. 7.

FIG. 5 is a front view of the insertion part 30 to which the elevator attachment 90 is attached. FIG. 6 is a figure viewing the insertion part 30 from the arrow direction VI in FIG. 5. FIG. 7 is a figure viewing the insertion part 30 from the arrow direction VII in FIG. 5. FIG. 8 is a partially sectional view of the insertion part 30 taken along the line VIII-VIII in FIG. 5. FIG. 9 illustrates the operation of the elevator 80. FIG. 10 is a partially sectional view of the insertion part 30 taken along the line X-X in FIG. 6. FIG. 11 is a partially sectional view of the insertion part 30 taken along the line XI-XI in FIG. 7.

Figure 12:
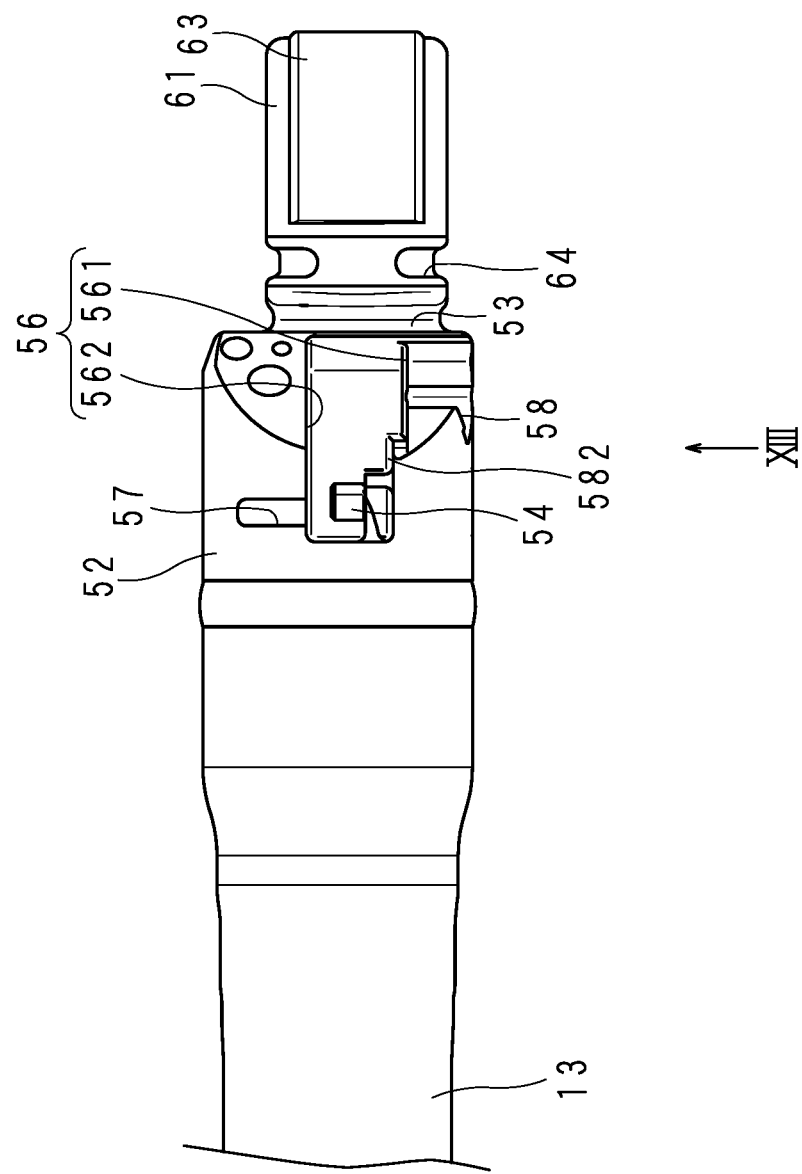
FIG. 12 is a front view of the insertion part from which the elevator attachment is detached.
Figure 13:
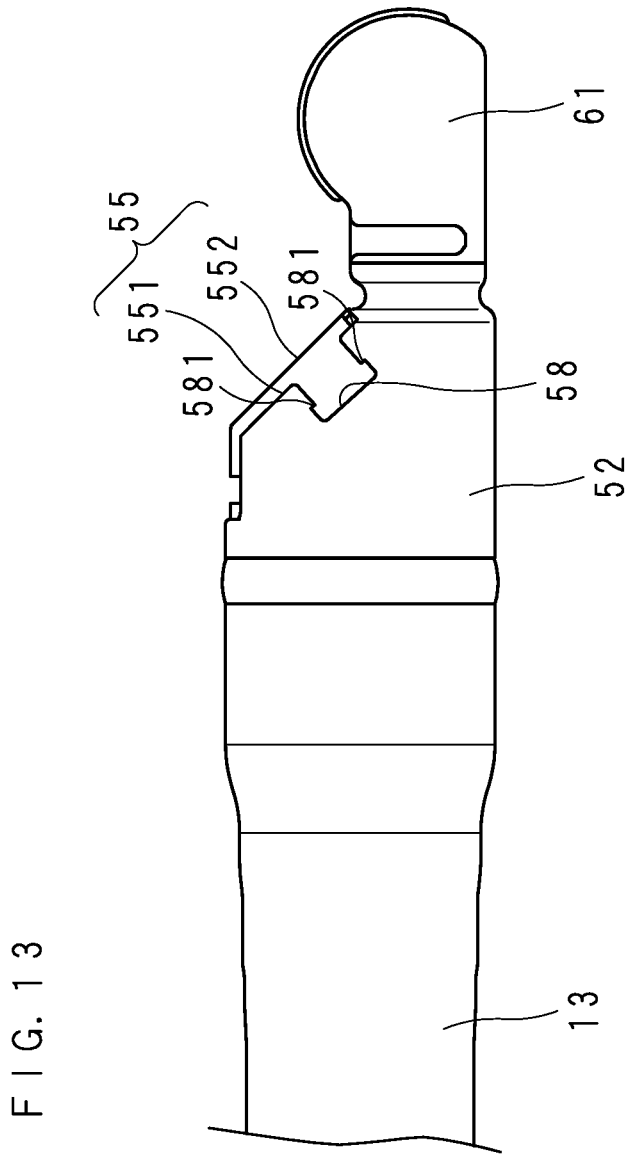
FIG. 13 is a figure viewing the insertion part from which the elevator attachment is detached from the arrow direction XIII in FIG. 12.

FIG. 12 is a front view of the insertion part 30 from which the elevator attachment 90 is detached. FIG. 13 is a figure viewing the insertion part 30 from which the elevator attachment 90 is detached from the arrow direction XIII in FIG. 12. In the cross sectional view from FIG. 8 to FIG. 11, the internal configuration of the distal end frame 52, the ultrasound probe 61 and the bending section 13 will not be illustrated.

As illustrated in FIG. 12, the first inner wall 561 has a stepped shape so as to be close to the second inner wall 562 toward the operation part side. As illustrated in FIG. 3 and FIG. 12, a prism-shaped lever 54 protrudes from a position of the first inner wall 561 close to the second inner wall 562 toward the second inner wall 562. The lever 54 pivots in conjunction with the manipulation of the elevator operation lever 21 by the user. The rotational axis of the lever 54, which penetrates the lever 54, is substantially perpendicular to the insertion direction. The structure of operating the lever 54 in conjunction with the elevator operation lever 21 is conventionally employed and will not be repeated.

In the case where the elevator attachment 90 is attached to the insertion part 30, the lever 54 and a lever connection part 81 provided in the elevator 80 are engaged with each other as illustrated in FIG. 8. The lever 54 pivots to also rotate the elevator 80 as illustrated in FIG. 9. The user operates the elevator operation lever 21 to make the elevator 80 pivot to thereby adjust the orientation of the treatment tool protruded toward the distal end side through the channel 34.

As illustrated in FIG. 10, the elevating part 83 has a thickness substantially the same as the space between the first plate 71 and the second plate 72. Thus, the treatment tool protruding from the channel 34 does not fall between the elevating part 83 and the first plate 71 or between the elevating part 83 and the second plate 72. A pivotable range of the elevator 80 is restricted by the stopper protrusion 729 and the connection part 74.

As illustrated in FIG. 3, FIG. 6 and FIG. 12, the groove-like engagement concave part 57 substantially perpendicular to the second inner wall 562 is provided on the periphery of the distal end frame 52. The engagement concave part 57 is linear.

As illustrated in FIG. 3 and FIG. 13, a holding groove 58 substantially perpendicular to the first inner wall 561 is provided on the first inclined surface 551. The holding groove 58 is a groove having a T-shaped cross section with the leg of the T directed toward the first inclined surface 551 and the cross bar of the T substantially parallel with the first inclined surface 551. Two substantially right-angled inner wall pawls 581 are provided so as to face each other at the portion where the leg and the cross bar of the T is combined.

As illustrated in FIG. 11, the inner wall pawl 581 and an engaging pawl 711 are engaged with each other to fix the holding body 70 with the distal end frame 52. The first inner wall 561 has a single-stepped portion 582 formed so as to be close to the second inner wall 562 at the bottom of the holding groove 58. The edge of the first plate 71 and the stepped portion 582 abut against each other or have a small clearance. Although not illustrated, the other one of the inner wall pawls 581 corresponding to the inner wall pawl 581 illustrated in FIG. 11 is also engaged with the other edge of the engaging pawl 711.

As illustrated in FIG. 5 and FIG. 10, the engagement protrusion 727 is engaged with the engagement concave part 57. The engagement protrusion 727 is engaged in a state where it is pressed against the distal end side surface of the engagement concave part 57, which fixes the holding body 70 with the distal end frame 52 by frictional force. As described above, the distal end frame 52 and the holding body 70 are engaged with each other at a total of three sites including the two inner wall pawls 581 and the engagement concave part 57.

Figure 14:
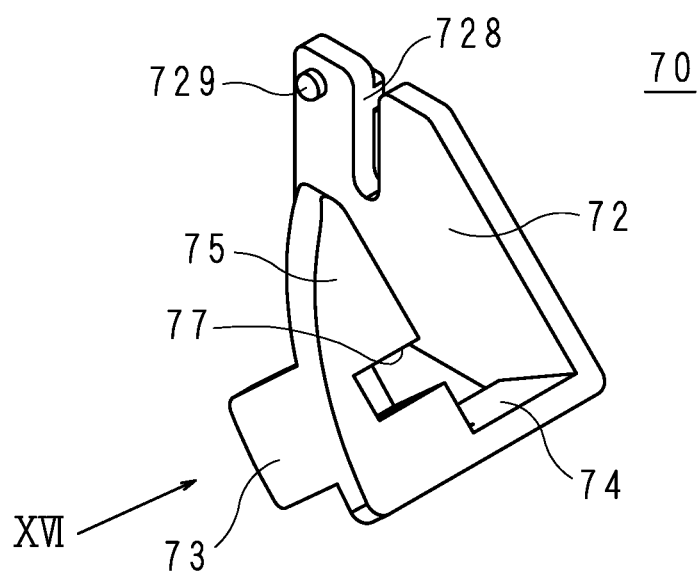
FIG. 14 is a perspective view of a holding body.
Figure 15:
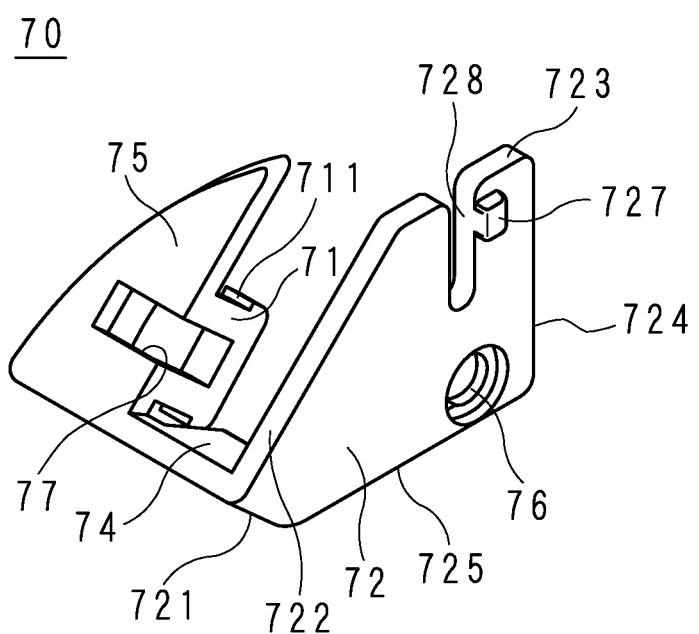
FIG. 15 is a perspective view of the holding body.
Figure 16:
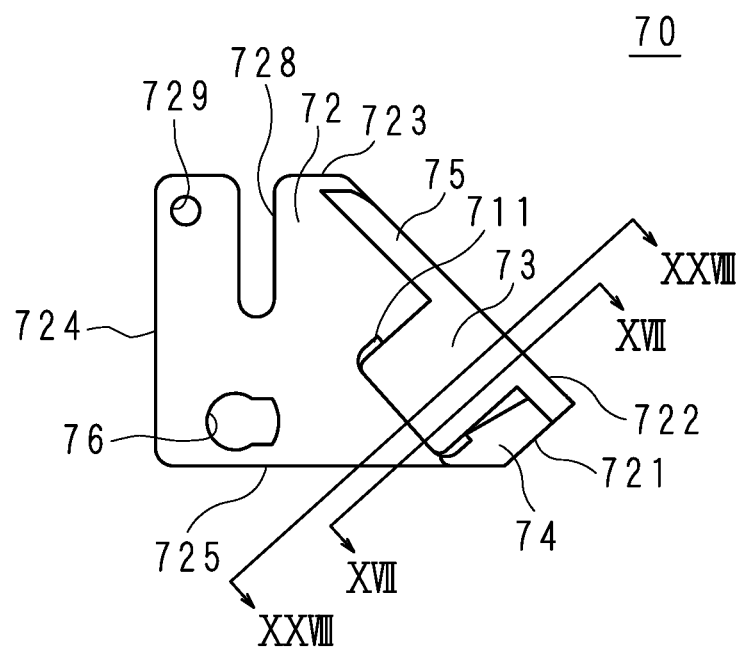
FIG. 16 is a figure viewing the holding body from the arrow direction XVI in FIG. 14.
Figure 17:
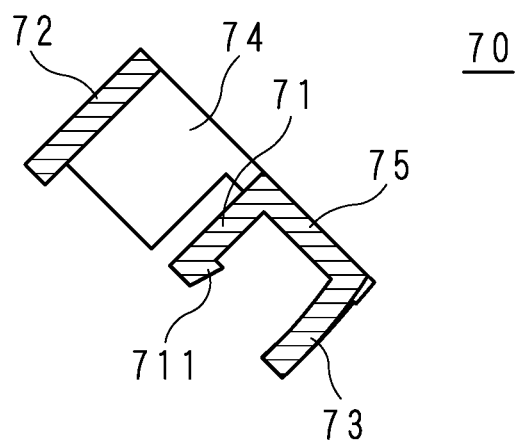
FIG. 17 is a sectional view of the holding body taken along the line XVII-XVII in FIG. 16.

FIG. 14 and FIG. 15 are perspective views of the holding body 70. FIG. 16 is a figure viewing the holding body 70 from the arrow direction XVI in FIG. 14. FIG. 17 is a cross-sectional view of the holding body 70 taken along the line XVII-XVII in FIG. 16. The configuration of the holding body 70 will be described with reference to FIG. 14 to FIG. 17.

An elevator attachment hole 76 is provided at a position in the vicinity of the fifth side 725 and close to the fourth side 724 of the second plate 72. The elevator attachment hole 76 has a circular hole a part of which is formed in a substantially U-shaped groove. The substantially U-shaped groove is provided at the periphery of the circular hole opposite to the fourth side 724 side. A counterboring circularly recessed on the side not facing the first plate 71 is provided at the perimeter of the elevator attachment hole 76.

The end surface on the first plate 71 side of the connection part 74 and the first plate 71 are away from each other by a distance corresponding to the thickness of the second plate 72. Thus, the elastic deformation of the first plate 71 to be described later is not hindered by the connection part 74.

Figure 18:
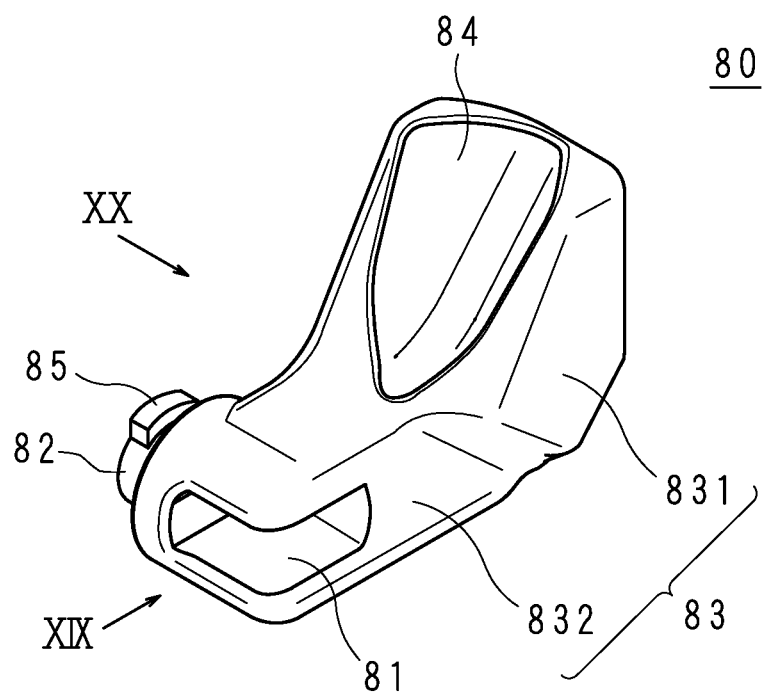
FIG. 18 is a perspective view of the elevator.
Figure 19:
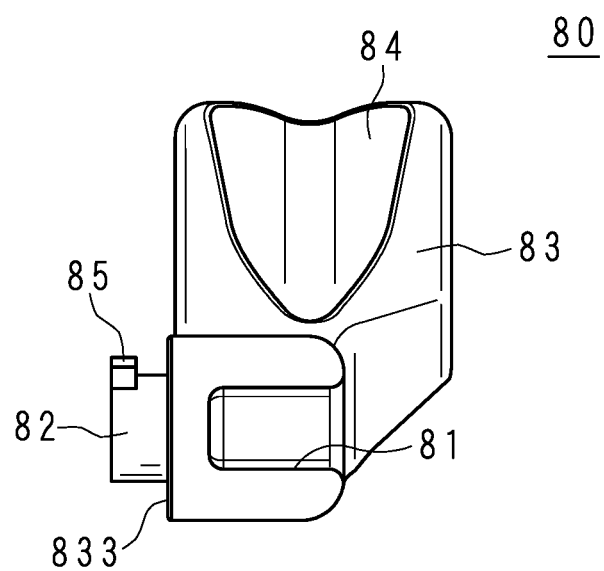
FIG. 19 is a figure viewing the elevator from the arrow direction XIX in FIG. 18.
Figure 20:
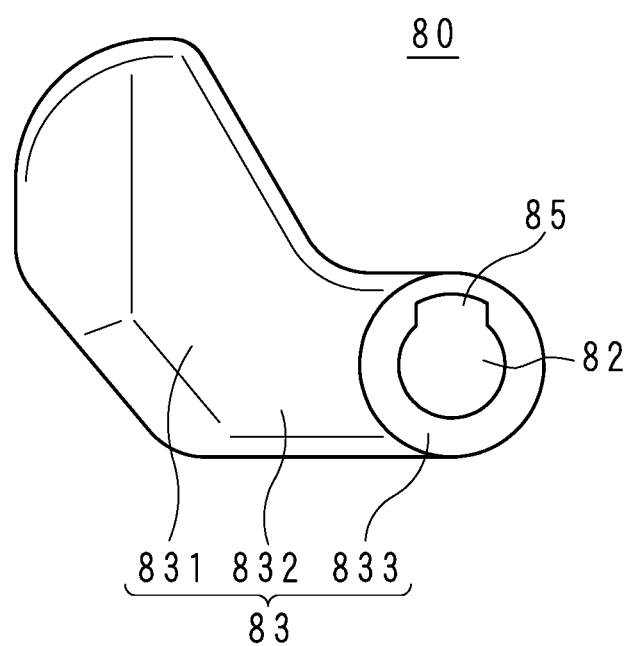
FIG. 20 is a figure viewing the elevator from the arrow direction XX in FIG. 18.

FIG. 18 is a perspective view of the elevator 80. FIG. 19 is a figure viewing the elevator 80 from the arrow direction XIX in FIG. 18. FIG. 20 is a figure viewing the elevator 80 from the arrow direction XX in FIG. 18. The structure of the elevator 80 will now be described with reference to FIG. 18 to FIG. 20.

As illustrated in FIG. 18 to FIG. 20, the elevator 80 has an elevator shaft 82 in addition to the elevating part 83 described above. The elevating part 83 is substantially L-shaped and has a first elevating part 831 having the recess 84 on one surface and a second elevating part 832 protruding from the edge of the first elevating part 831 on the same side as the surface of the first elevating part 831 that has the recess 84.

The surface of the first elevating part 831 that has the recess 84 is smoothly continuous to the one surface of the adjacent second elevating part 832. On a surface of the second elevating part 832 adjacent to the surface continuous to the surface that has the recess 84 is provided with a circular part 833 that protrudes by one step from the one surface adjacent to the first elevating part 831.

The lever connection part 81 is a recess opened to two directions including a direction along an end surface opposite to the side where the second elevating part 832 is continuous to the first elevating part 831 and a direction along a surface opposite to the circular portion 833 side. The interior of the lever connection part 81 has a shape of a substantially rectangular parallelepiped and forms an opened surface at the adjacent two sides.

The elevator shaft 82 has a columnar shape that protrudes from the one surface of the second elevating part 832. The central axis of the elevator shaft 82 penetrates the lever connection part 81. A substantially rectangular plate-like shaft stopper 85 protrudes from the periphery of the elevator shaft 82 near the edge thereof. The protruding direction of the shaft stopper 85 is perpendicular to the two inner surfaces of the lever connection part 81 that face each other and is directed toward one of the two inner surfaces closer to the recess 84.

Figure 21:
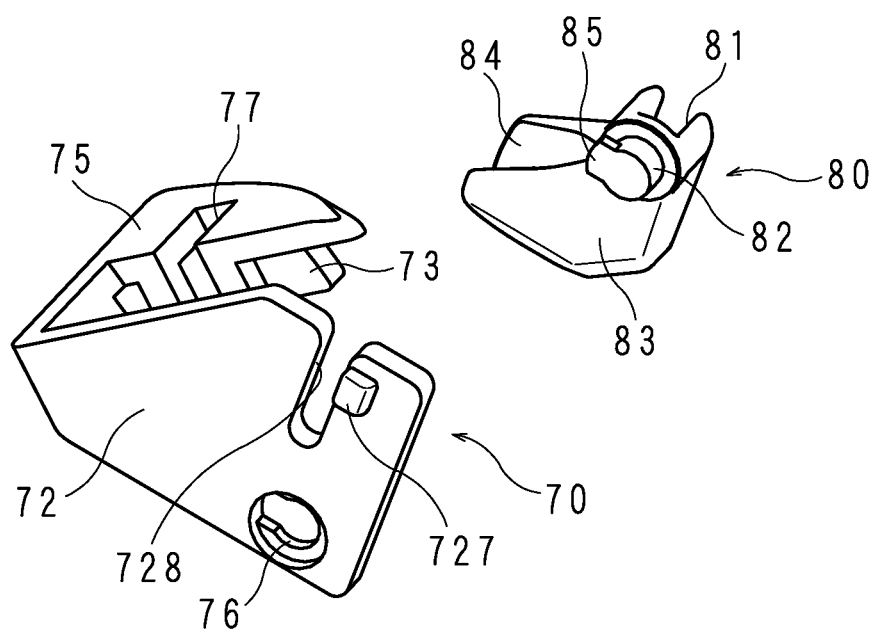
FIG. 21 illustrates an assembly method of the elevator attachment.
Figure 22:
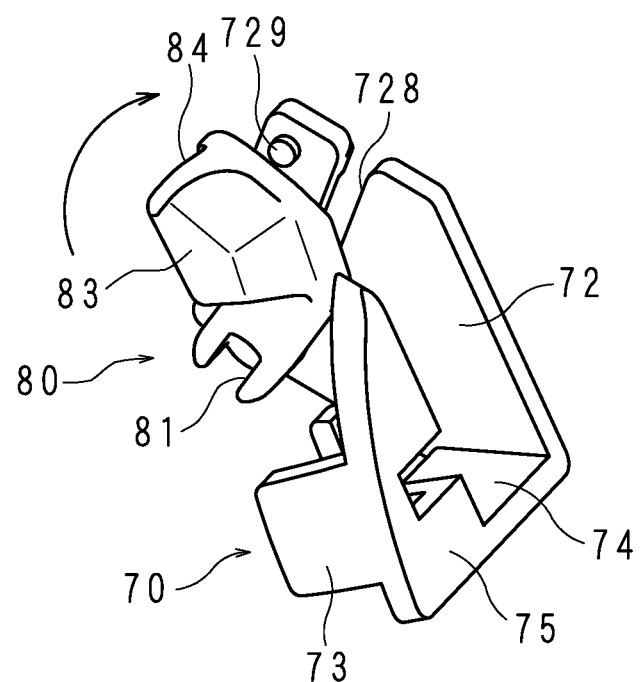
FIG. 22 illustrates the assembly method of the elevator attachment.
Figure 23:
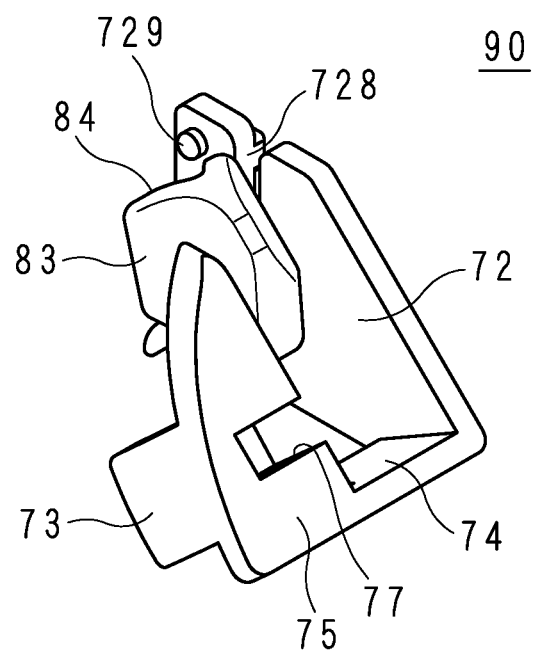
FIG. 23 illustrates the assembly method of the elevator attachment.

FIG. 21 to FIG. 23 illustrate an assembly method of the elevator attachment 90. The structure of the elevator attachment 90 and the assembly method will now be described with reference to FIG. 21 to FIG. 23.

As illustrated in FIG. 21, the elevator shaft 82 is inserted into the elevator attachment hole 76 from the third plate 73 side in a state where the substantially U-shaped groove provided in the elevator attachment hole 76 and the shaft stopper 85 are aligned. As illustrated in FIG. 22, the elevator 80 pivots clockwise in FIG. 22 about the elevator shaft 82. The pivoting causes misalignment between the substantially U-shaped groove and the shaft stopper 85, so that the elevator 80 does not come off from the holding body 70.

The vicinity of the stopper protrusion 729 of the second plate 72 is bent toward the depth direction in FIG. 22 to place the elevating part 83 between the stopper protrusion 729 and the connection part 74 as illustrated in FIG. 23. Hence, the assembly of the elevator attachment 90 is completed.

It is desirable that the circular part 833 and a part of the second plate 72 that abuts against the circular part 833 are smooth surfaces. This allows the elevator 80 to smoothly pivot. The circular part 833 can prevent the elevating part 83 from being in contact with the second plate 72 during pivoting.

The division slot 728 formed on the second plate 72 allows the second plate 72 easily bend and allows the elevator 80 to easily shift from the state in FIG. 22 to the state in FIG. 23. After the elevator attachment 90 is attached to the insertion part 30, the second plate 72 is retained in the elevator recess 56 without being bent. Accordingly, the pivotable range of the elevator 80 is restricted by the stopper protrusion 729 and the connection part 74.

Figure 24:
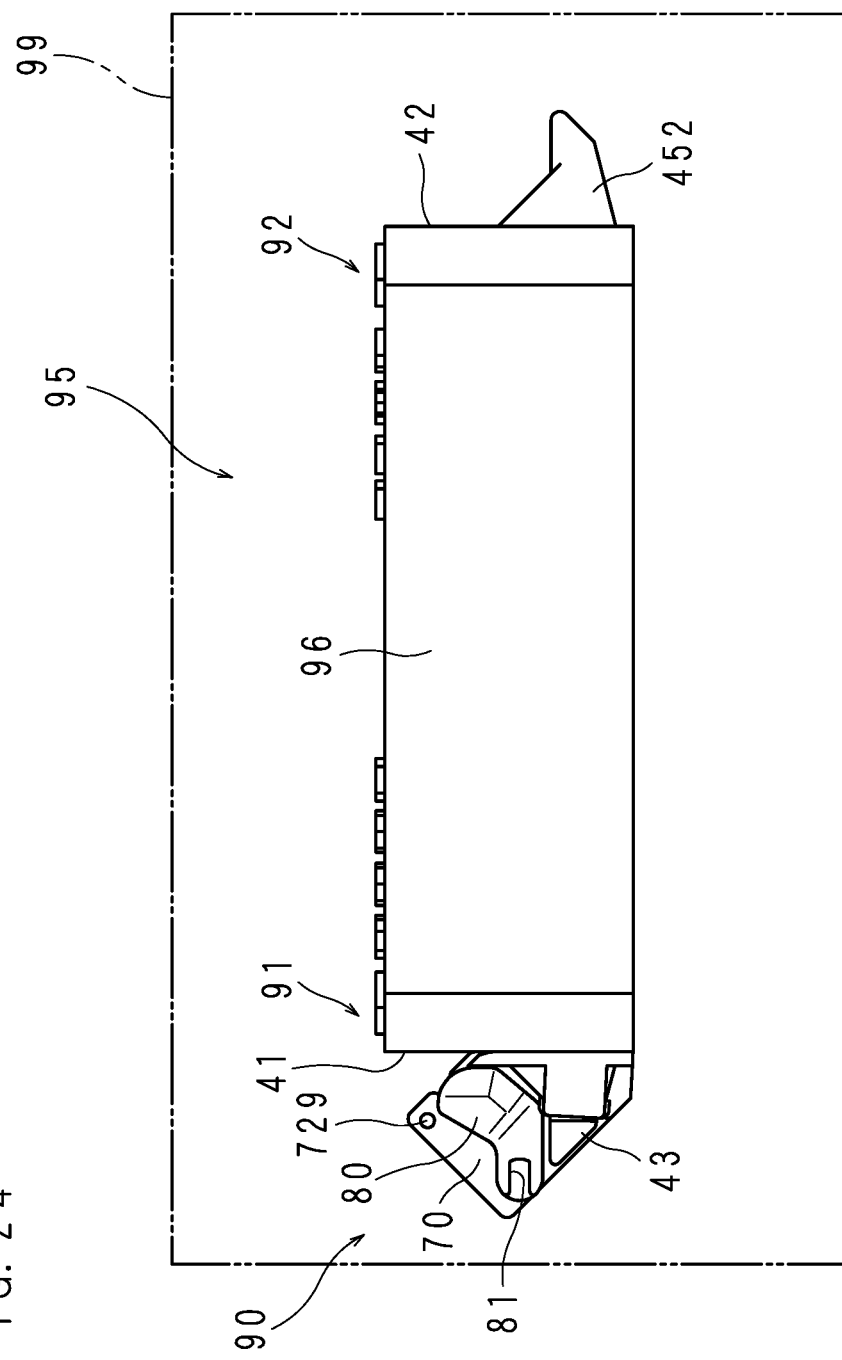
FIG. 24 illustrates a supply manner of the elevator attachment.

FIG. 24 illustrates a supply manner of the elevator attachment 90. The elevator attachment 90 is enclosed in an individual packaging such as a sterile package 99 or the like one by one in a state where it is attached to a removable jig 95 and is supplied while being sterilized by any sterilization means such as electron beam sterilization.

Figure 25:
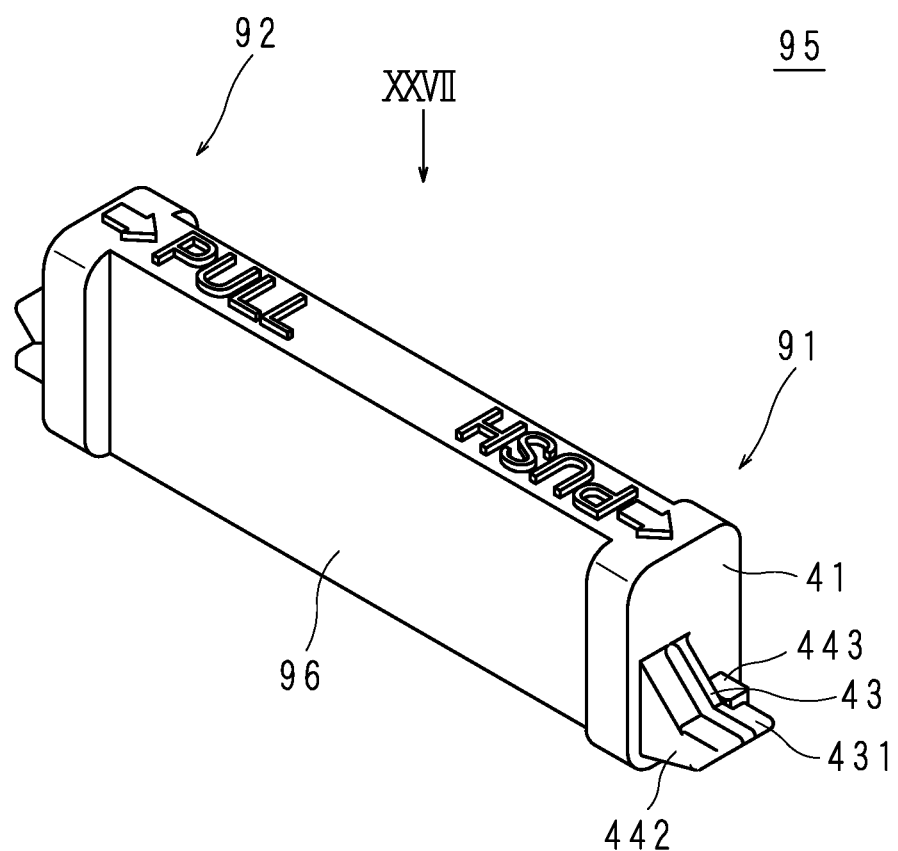
FIG. 25 is a perspective view of a removable jig.
Figure 26:
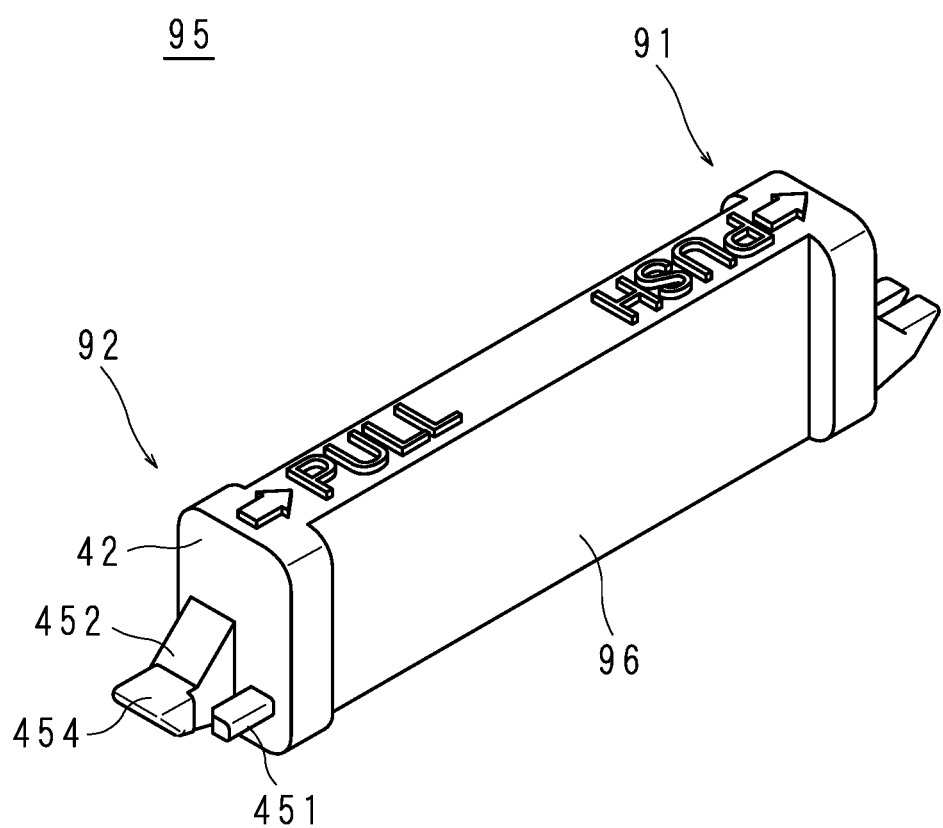
FIG. 26 is a perspective view of the removable jig.
Figure 27:
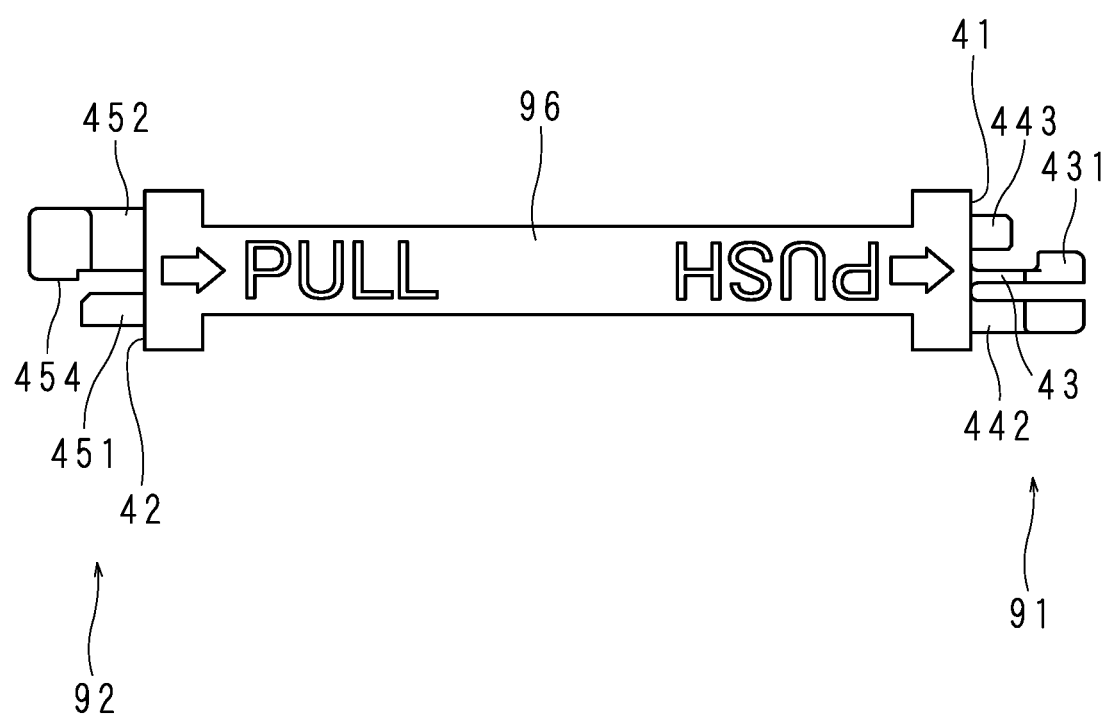
FIG. 27 is a figure viewing the removable jig from the arrow direction XXVII in FIG. 25.

FIG. 25 and FIG. 26 are perspective views of the removable jig 95. FIG. 27 is a figure viewing the removable jig 95 from the arrow direction XXVII in FIG. 25. The structure of the removable jig 95 will now be described with reference to FIG. 24 to FIG. 27.

The removable jig 95 includes a prism-shaped holding part 96 having a first jig 91 at one end and a second jig 92 at the other end. As illustrated in FIG. 24, the elevator attachment 90 is supplied while being attached to the first jig 91. The user attaches the elevator attachment 90 to the endoscope 10 using the first jig 91. The second jig 92 is used when the elevator attachment 90 is removed from the endoscope 10 after completion of endoscopy.

The holding part 96 is thick and long enough for the user who wears a medical glove to easily handle. The holding part 96 includes characters of "PUSH" on the first jig 91 side and "PULL" on the second jig 92 side. This allows the user to easily discriminate the first jig 91 side from the second jig 92 side. These characters are embossed and serve as a non-slip when the user performs attachment and removal work of the elevator attachment 90.

The structure of the first jig 91 will be described with reference to FIG. 24, FIG. 25 and FIG. 27. From a first abutting portion 41 located on an end surface of the holding part 96, a second retention projection 442, an elastic plate 43 and a third retention projection 443 project in this order.

The second retention projection 442 has a platelike shape of a triangle with the bottom connected to the first abutting portion 41 and with a side extending from the vertex connected to another small triangle. The elastic plate 43 has approximately the same shape as the second retention projection 442 in a plan view. The second retention projection 442 and the elastic plate 43 are arranged in parallel to each other to have a space in the direction of the thickness at an approximately the same position in a plan view.

The elastic plate 43 has a first retention projection 431 that projects on the third retention projection 443 side at its end. The third retention projection 443 is a quadratic prism having one side surface arranged in parallel with a main surface of the elastic plate 43. The end surface of the third retention projection 443 is closer to the first abutting portion 41 than the edge of the first holding projection 431 on the first abutting portion 41 side.

The structure of the second jig 92 will now be described with reference to FIG. 24, FIG. 26 and FIG. 27. A first projection 451 and a second projection 452 project from a second abutting portion 42 located on the other end surface of the holding part 96.

The second projection 452 is platelike having a shape substantially the same as the second holding projection 442 in a plan view. The thickness of the second projection 452 is substantially the same as a total of the thickness of the second retention projection 442, the elastic plate 43 and the space between the second retention projection 442 and the elastic plate 43.

The second projection 452 has, on its edge, a fourth retention projection 454 that projects toward the first projection 451 side. The first projection 451 has a prism shape having one side surface in parallel to a main surface of the second projection 452. The transverse cross section of the first projection 451 is substantially the same as that of the third retention projection 443. The end surface of the first projection 451 is located closer to the second abutting portion 42 than the edge of the fourth retention projection 454 on the second abutting portion 42 side.

Figure 28:
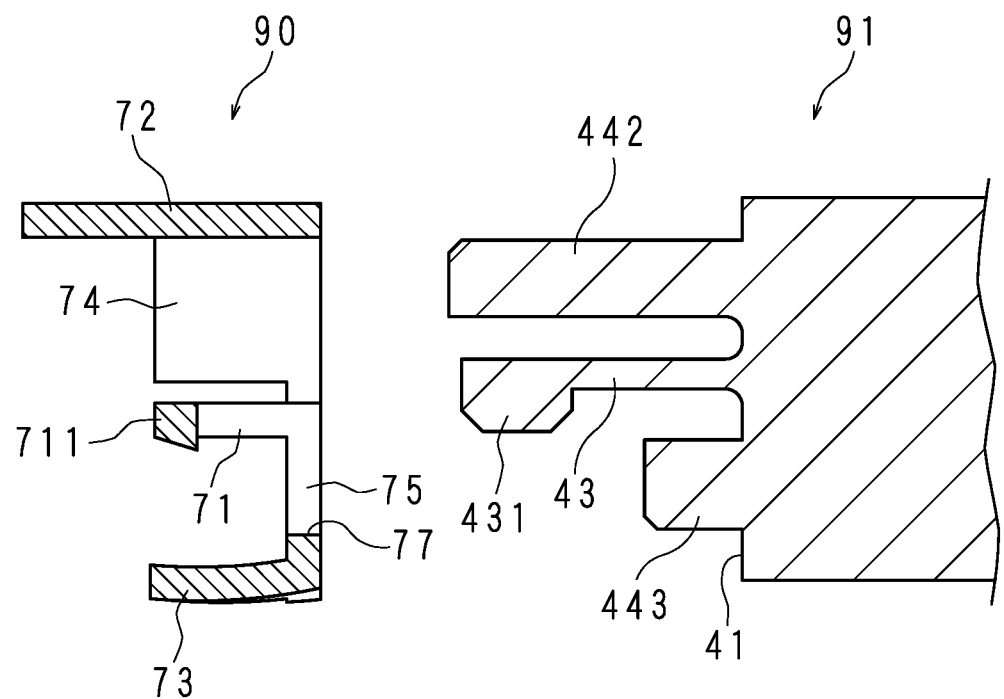
FIG. 28 illustrates a method of attaching the elevator attachment to a first jig.
Figure 30:
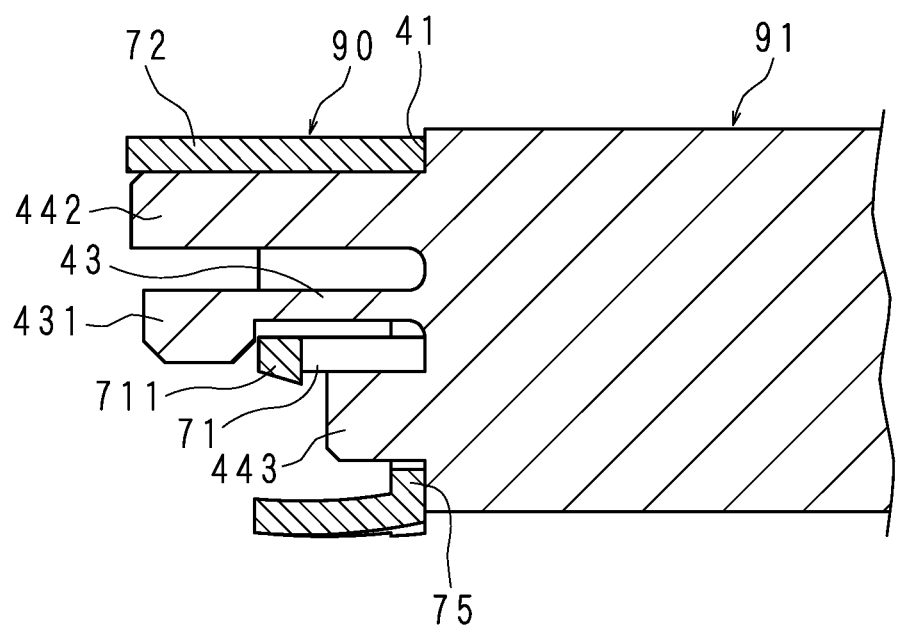
FIG. 30 illustrates a method of attaching the elevator attachment to the first jig.

FIG. 28 to FIG. 30 illustrate a method of attaching the elevator attachment 90 to the first jig 91. FIG. 28 to FIG. 30 illustrate cross sections taken along the line XXVIII-XXVIII in FIG. 16.

As illustrated in FIG. 28, the elevator attachment 90 directs the inclined surface plate 75 side thereof toward the first jig 91 and is held with the inclined surface plate 75 parallel with the first abutting portion 41. The second retention projection 442 and the elastic plate 43 are inserted to the space between the first plate 71 and the second plate 72.

As illustrated in FIG. 29, the elastic plate 43 is pressed by the first plate 71 to deform toward the second retention projection 442 side. The third retention projection 443 is inserted into the cutaway portion 77.

As illustrated in FIG. 30, the first retention projection 431 is inserted deeper than the edge of the first plate 71 to elastically restore the elastic plate 43. The end surface of the first retention projection 431 on the first-abutting-portion 41 side is in contact with the edge surface of the first plate 71. The inclined surface plate 75 and the first abutting portion 41 abut against each other. The second plate 72 is in contact with a side surface of the second retention projection 442 while the inner surface of the cutaway portion 77 is in contact with a side surface of the third retention projection 443.

The elevator attachment 90 is thus fixed to the first jig 91. In place of making contact, the contact portions described above may have gaps to such an extent that they do not interfere with a work of the succeeding processes.

As illustrated in FIG. 24 and FIG. 25, the elevator 80 is held with the recess 84 closer to the stopper protrusion 729 by the elastic plate 43 and the edge portion of the second retention protrusion 442. The lever connection part 81 is held while facing the opening at the end facing toward the longitudinal direction of the holding part 96.

As described with reference to FIG. 24, the elevator attachment 90 is enclosed in the sterile package 99 or the like one by one in a state where it is attached to the removable jig 95 and supplied to a medical institution in a sterilized state by any sterilization means such as electron beam sterilization and so forth.

The sterilization may be conducted by individual medical institutions before use of the elevator attachment 90. In such a case, enclosure of the elevator attachment 90 in the sterile package 99 may be conducted at a medical institution. The attachment of the elevator attachment 90 to the removable jig 95 described with reference to FIG. 28 to FIG. 30 may be conducted at a medical institution.

FIG. 31 to FIG. 35 illustrate a method of attaching the elevator attachment 90 to the endoscope 10. FIG. 32 to FIG. 35 illustrate cross sections taken along the line XXVIII-XXVIII in FIG. 16 as in FIG. 28 to FIG. 30.

The user operates the elevator operation lever 21 to cause the lever 54 to have an orientation obtained when the elevator 80 is raised. This operation allows the lever 54 and the lever connection part 81 to be aligned with each other.

Figure 31:
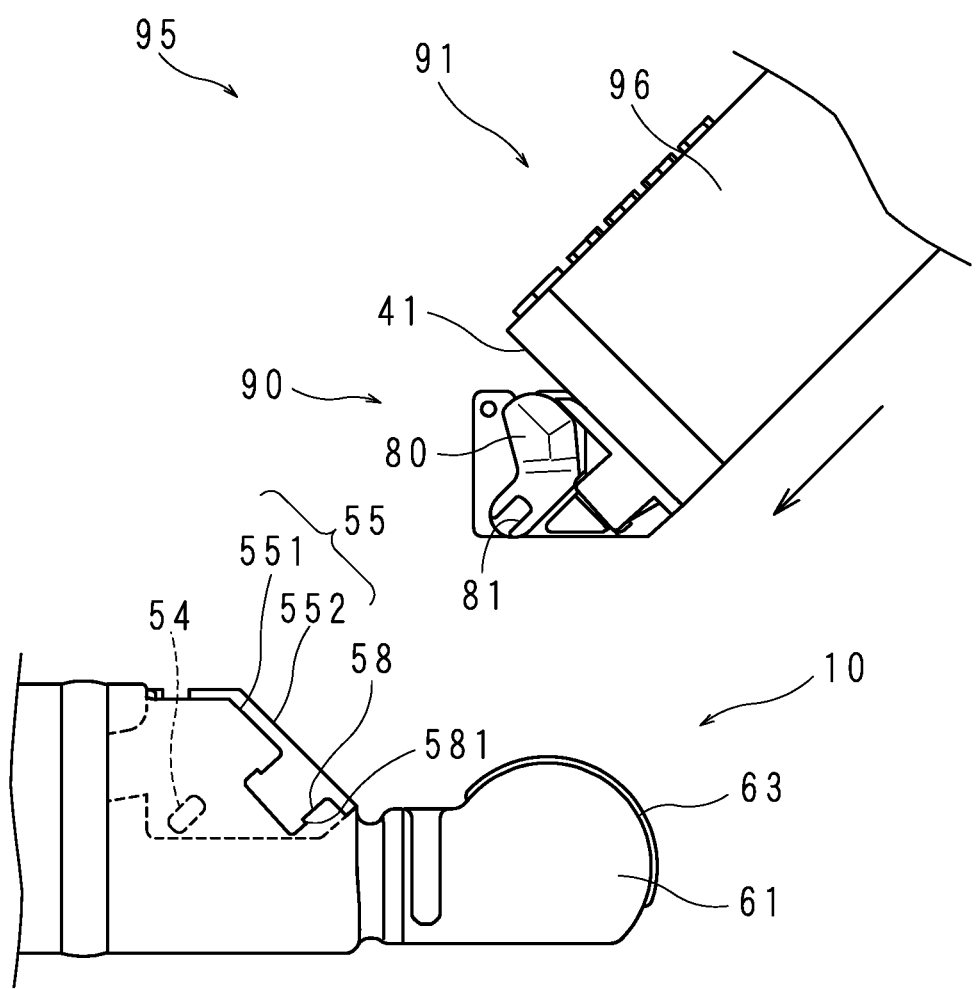
FIG. 31 illustrates a method of attaching the elevator attachment to the endoscope.
Figure 32:
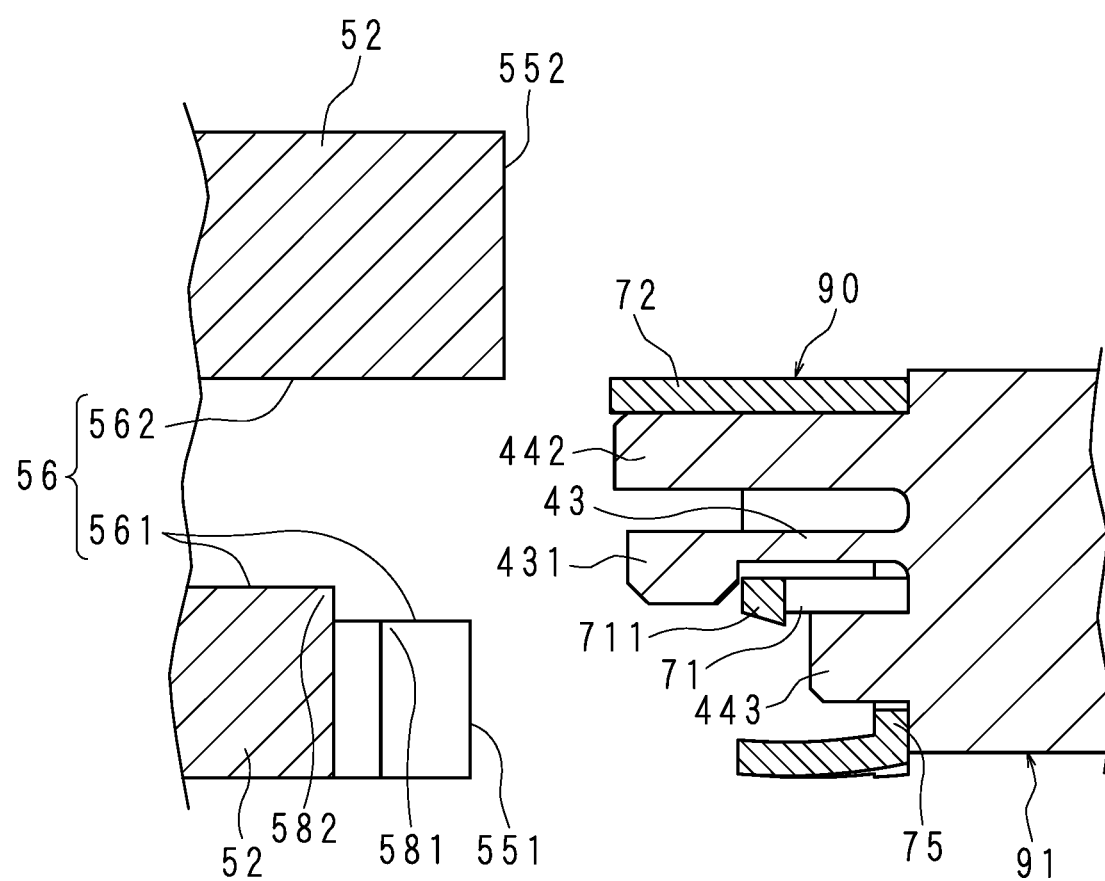
FIG. 32 illustrates a method of attaching the elevator attachment to the endoscope.

As illustrated in FIG. 31 and FIG. 32, the user holds the removable jig 95 attached with the elevator attachment 90 such that the first abutting portion 41 is parallel with the inclined surface 55. The user presses the removable jig 95 into the endoscope 10 such that the elevator 80 fits into the elevator recess 56.

Figure 33:
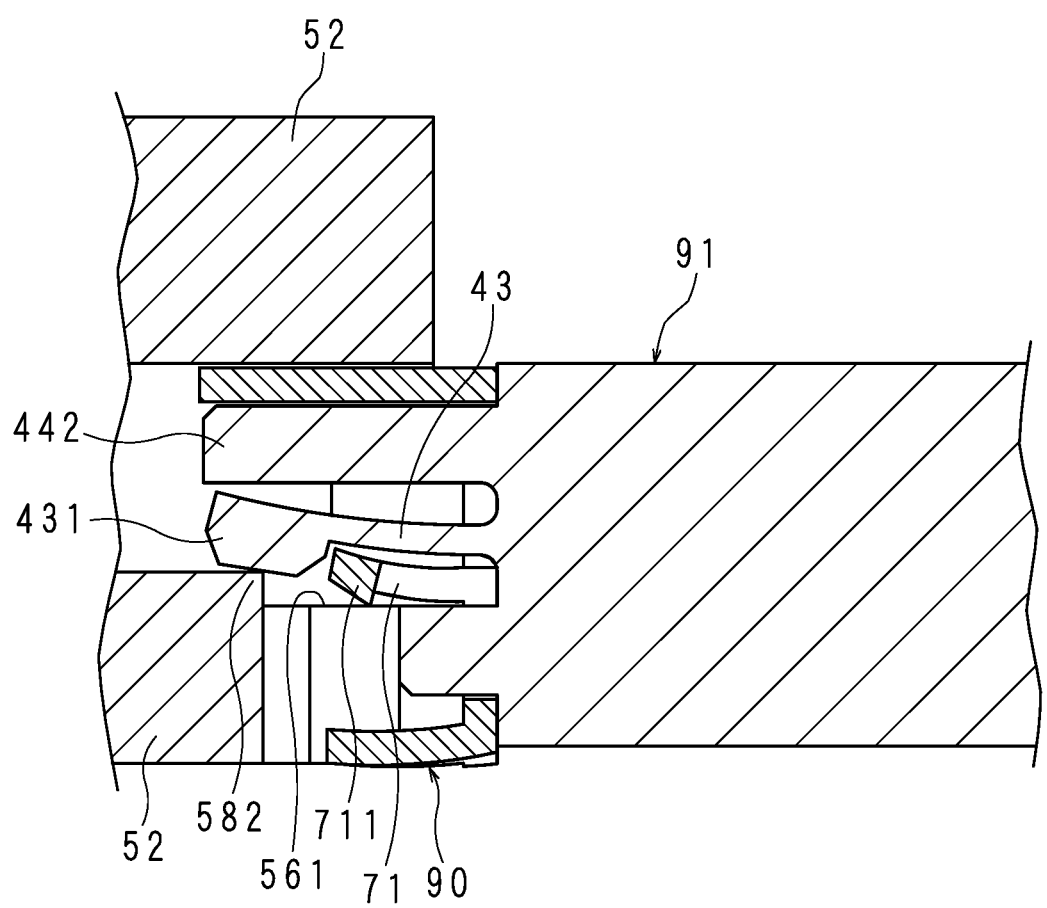
FIG. 33 illustrates a method of attaching the elevator attachment to the endoscope.

As illustrated in FIG. 33, the first retention projection 431 is pressed by the stepped portion 582 to elastically deform the elastic plate 43 toward the second retention protrusion 442 side. Both edges of the engaging pawl 711 are pressed by the first inner wall 561 at the edge of the holding groove 58 to elastically deform the first plate 71 toward the second retention projection 442 side.

Figure 34:
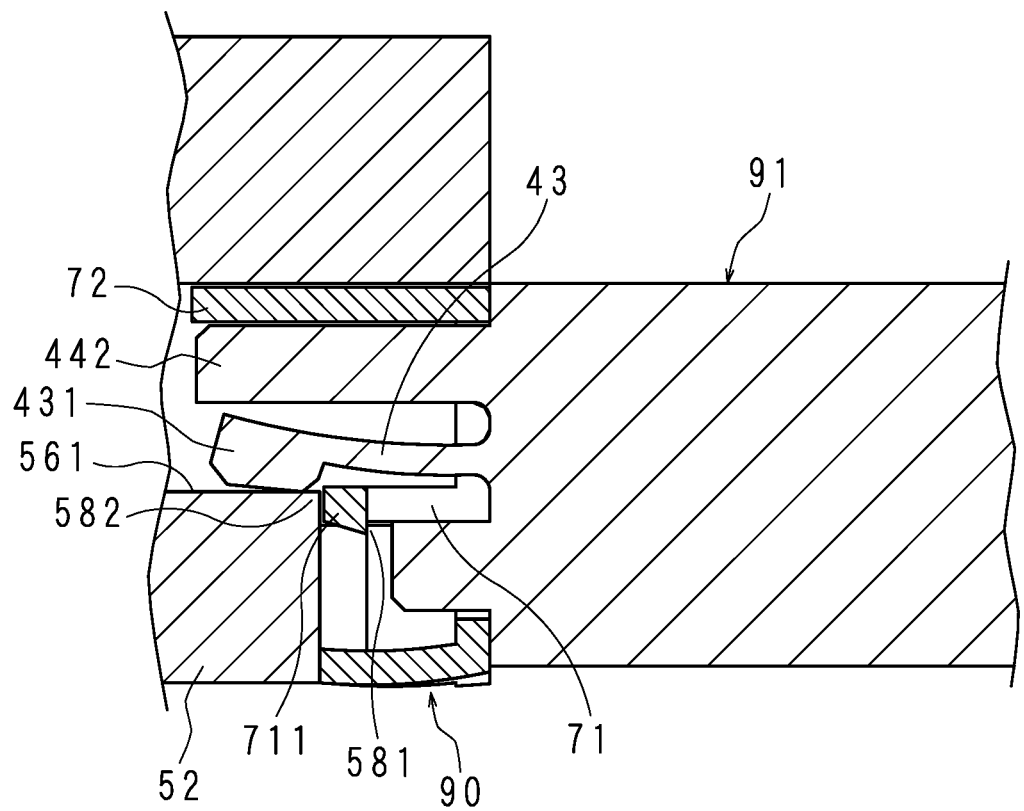
FIG. 34 illustrates a method of attaching the elevator attachment to the endoscope.

As illustrated in FIG. 34, the engaging pawl 711 is inserted deeper than the inner wall pawl 581 to elastically restore the first plate 71. The engaging pawl 711 and the inner wall pawl 581 are engaged with each other. The surface of the first plate 71 on the second plate 72 side and the first inner wall 561 deeper than the stepped portion 582 are substantially on the same level.

Although not illustrated, the part of the second plate 72 more toward the engagement protrusion 727 than the division slot 728 is elastically deformed toward the elevator 80 side to cause the engagement protrusion 727 to engage with the engagement concave part 57 as described with reference to FIG. 5 and FIG. 10. Since the lever 54 and the lever connection part 81 are aligned with each other, the lever 54 is inserted into the lever connection part 81.

Figure 35:
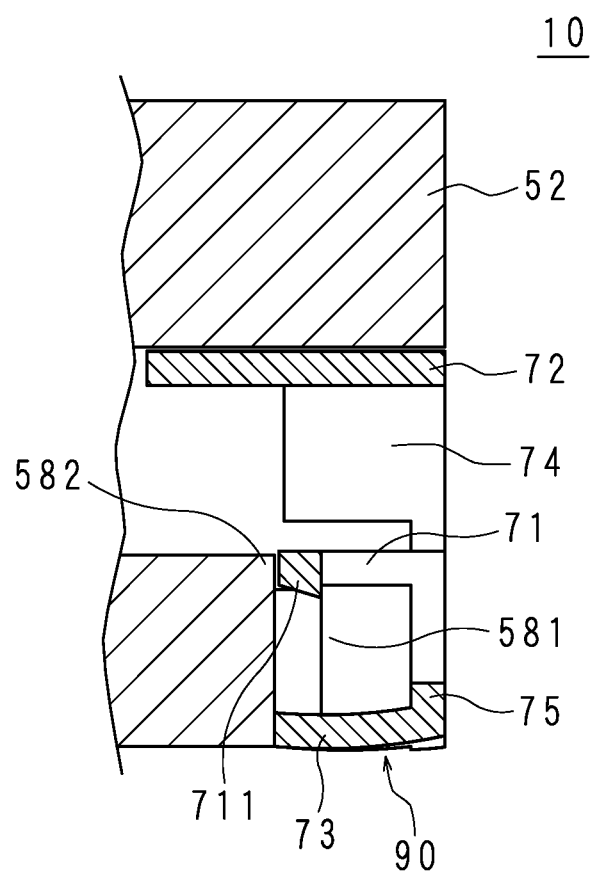
FIG. 35 illustrates a method of attaching the elevator attachment to the endoscope.

The user pulls out the removable jig 95 from the state in FIG. 34 to separate the elevator attachment 90 from the first jig 91 as illustrated in FIG. 35. As described with reference to FIG. 2, the endoscope 10 is in a state of being attached with the elevator attachment 90. The attachment work of the elevator attachment 90 to the endoscope 10 is thus completed.

The user can easily attach the elevator attachment 90 to the endoscope 10 by using the removable jig 95. The removable jig 95 is larger in comparison with the elevator attachment 90, so that handling such as taking out from the sterile package 99 or the like is easy.

Due to an excessive force applied to the elevator attachment 90 and the endoscope 10 during an attachment work, damage to one or both of them can be prevented. The medical glove worn by the user can be prevented from having a hole during an attachment work.

It is noted that the elevator attachment 90 may be attached to the endoscope 10 without using the removable jig 95. The user inserts the elevator attachment 90 into the elevator recess 56 while pressing the elevator 80 with a finger and holding it in a proper orientation. The user presses the inclined surface plate 75 to cause the first plate 71 to be pressed and elastically deformed, which engages the engaging pawl 711 with the inner wall pawl 581.

Figure 36:
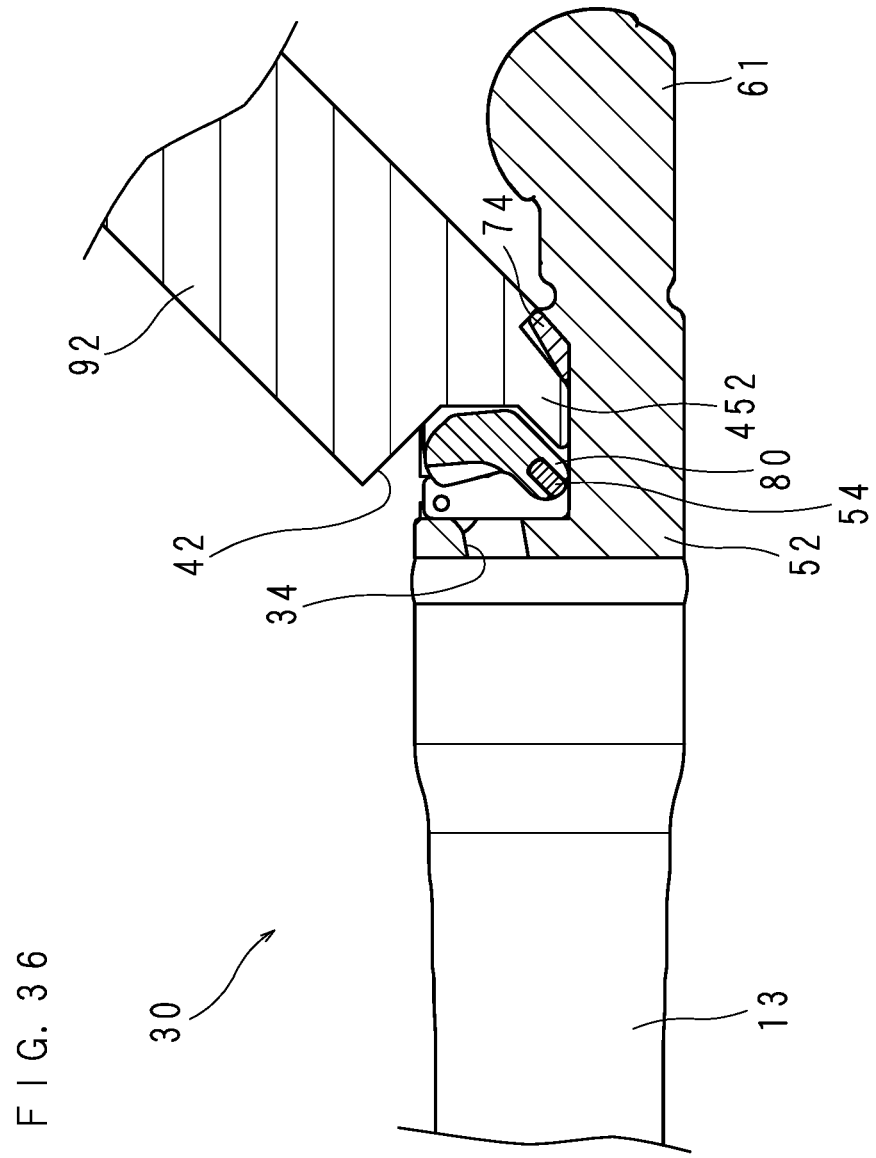
FIG. 36 illustrates a method of removing the elevator attachment from the endoscope.
Figure 37:
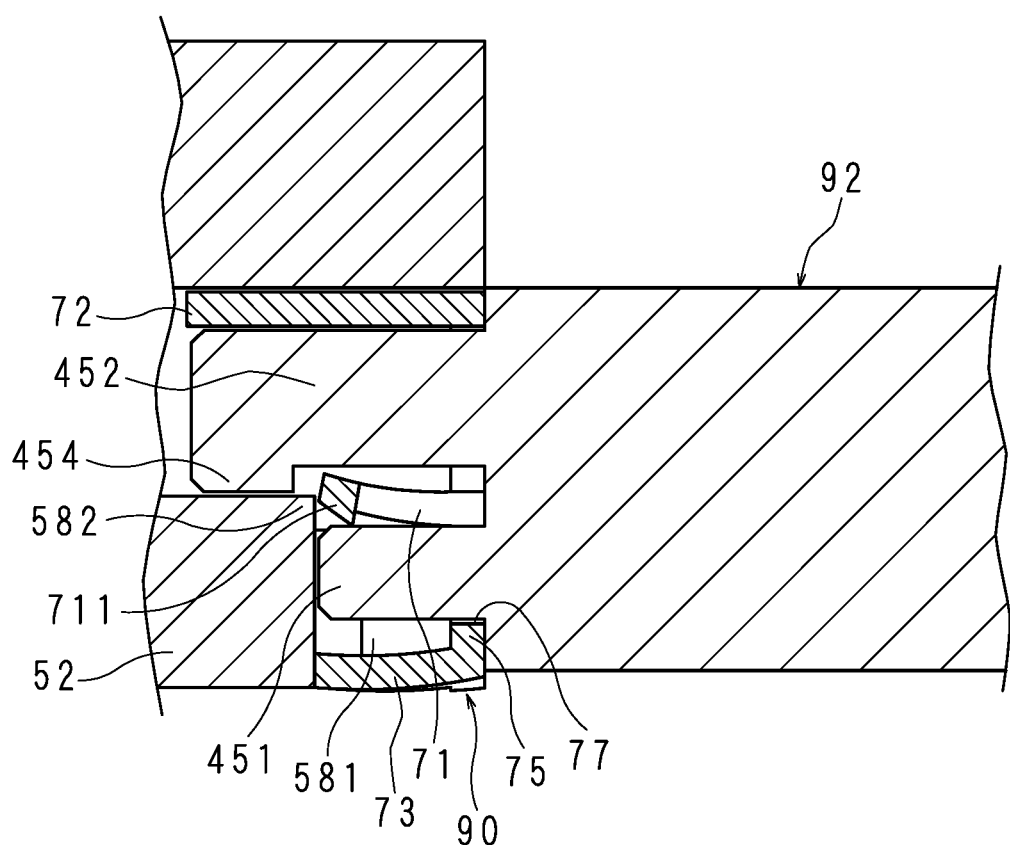
FIG. 37 illustrates a method of removing the elevator attachment from the endoscope.
Figure 38:
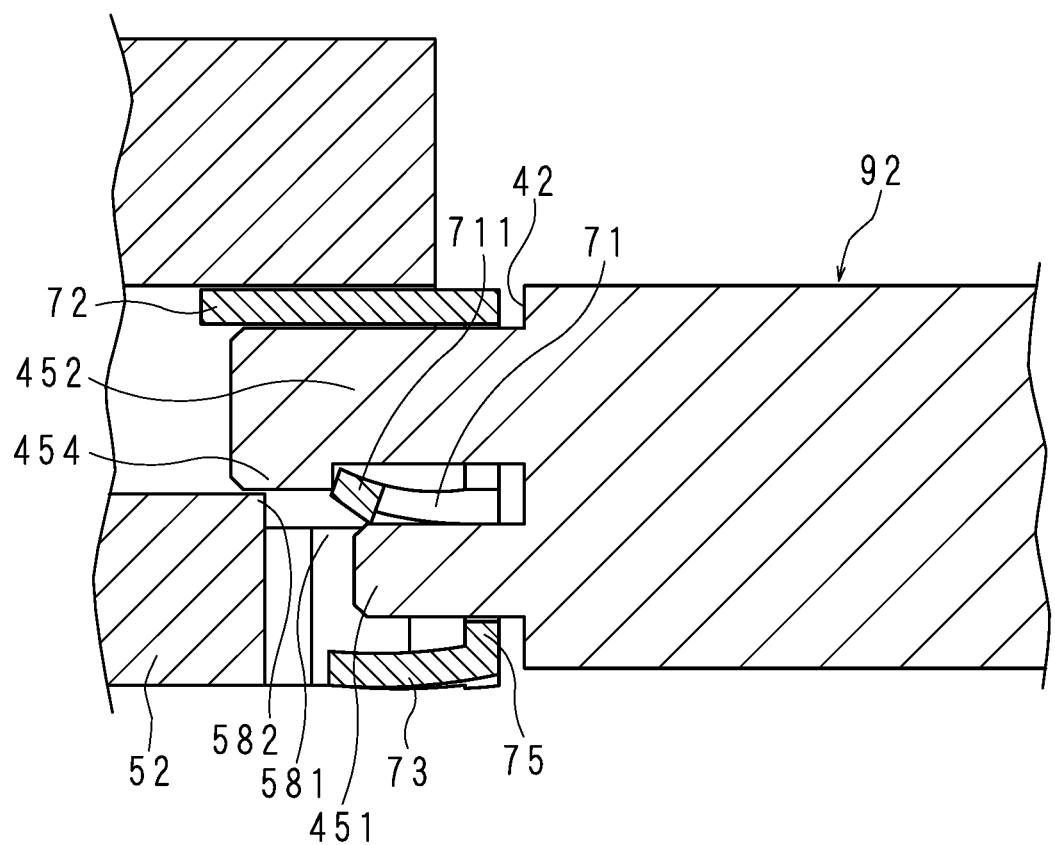
FIG. 38 illustrates a method of removing the elevator attachment from the endoscope.
Figure 39:
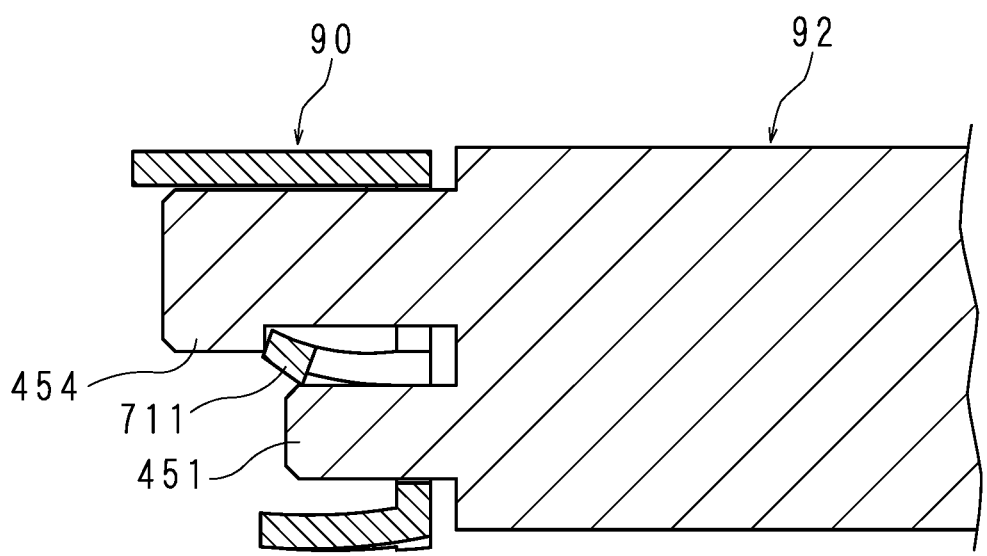
FIG. 39 illustrates a method of removing the elevator attachment from the endoscope.

FIG. 36 to FIG. 39 illustrate a method of removing the elevator attachment 90 from the endoscope 10. FIG. 36 illustrates a cross section taken along the line VIII-VIII in FIG. 5 as in FIG. 8. FIG. 37 to FIG. 39 illustrate a cross section taken along the line XXVIII-XXVIII in FIG. 16 as in FIG. 28 to FIG. 30.

As illustrated in FIG. 36, the user inserts the edge of the second projection 452 into the space between the elevator 80 and the connection part 74 to abut the second abutting portion 42 against the inclined surface plate 75. The elevator 80 pivots by the edge of the second projection 452 to cause the lever 54 and the lever connection part 81 to be aligned with each other as in a state described with reference to FIG. 31.

As illustrated in FIG. 37, the first projection 451 is inserted into the cutaway portion 77. The engaging pawl 711 is pressed by the first projection 451 to elasitcally deform the first plate 71 toward the second projection 452 side, which separates the engaging pawl 711 from the inner wall pawls 581.

The user pulls out the removable jig 95 in the state in FIG. 37 to bring the end surface of the first plate 71 in contact with the fourth retention projection 454 as illustrated in FIG. 38. Although not illustrated, the part of the second plate 72 more toward the engagement protrusion 727 than the division slot 728 is elastically deformed toward the elevator 80 side to release the engagement between the engagement protrusion 727 and the engagement concave part 57. As illustrated in FIG. 39, the elevator attachment 90 in the state where it is fixed on the second jig 92 comes off the endoscope 10.

Since the first plate 71 is deformed by being pressed by the first projection 451, the elevator attachment 90 does not come off the removable jig 95. The user discards the elevator attachment 90 after use together with the removable jig 95.

The user can easily remove the elevator attachment 90 from the endoscope 10 by using the removable jig 95. Since the removed elevator attachment 90 cannot be separated from the removable jig 95, erroneous reusing of the elevator attachment 90 can be prevented.

The use of the removable jig 95 can prevent the user from erroneously damaging the endoscope 10 during the removal work of the elevator attachment 90. This can also prevent the medical glove worn by the user from having a hole during the removal work.

The first jig 91 and the second jig 92 form the removable jig 95 as one piece, so that the user can remove the elevator attachment 90 after use from the endoscope 10 by using the removable jig 95 to which the elevator attachment 90 has been attached. In other words, this eliminates the user having to separately prepare another jig for removing the elevator attachment 90.

A method using the endoscope 10 according to the present embodiment will now be summarized. The endoscope 10 is stored in a state of having been cleaned or the like. The user takes out the removable jig 95 attached with the elevator attachment 90 from the sterile package 99. The user attaches the elevator attachment 90 to the endoscope 10 according to the procedure described with reference to FIG. 31 to FIG. 35.

The user connects the first connector 16 to the video processor, the light source device, the display device and so forth. The user connects the second connector 17 to the ultrasound processor.

The user supplies water from a balloon water supply/drain hole provided in the balloon water supply and drain groove 64 by operating the water supply button 25 to make a balloon channel (not illustrated) be filled with water. The user puts the balloon 98 with an O-ring at its opening on the ultrasound probe 61, and fits and fixes the O-ring into the balloon fixing groove 53. Note that the elevator attachment 90 may be attached after the balloon 98 is put on.

The user makes water flow through the balloon water supply/drain hole by operating the water supply button 25 to swell the balloon 98 as indicated by a two-dot chain line in FIG. 7. The user confirms that the balloon 98 is properly attached by swelling the balloon 98. Thereafter, the user drains the water from the balloon water supply/drain hole by operating the water supply button 25 to shrink the balloon 98 and make the balloon 98 in closely contact with the ultrasound probe 61.

The user inserts the insertion part 30 through the mouth of a subject for examination. While viewing a video image photographed via the observation window 36, the user guides the distal end of the insertion part 30 to a target site. The user applies the ultrasound wave transmitting and receiving surface 63 to the target site via the balloon 98 to perform ultrasonography. The user suitably change the size of the balloon 98 by operating the water supply button 25 to capture the target site at a desired position on the ultrasound image.

The user uses a treatment tool such as a puncture needle or the like such that it protrudes from the distal end frame 52 through the channel 34. Since the treatment tool protrudes along the ultrasound scanning surface, the user can observe the positional relation between the distal end of the treatment tool and the lesion or the like with an ultrasound image. The user pivots the elevator 80 by operating the elevator operation lever 21 or the like to guide the distal end of the treatment tool at a desired position.

After completion of a necessary treatment and so forth, the user pulls out the treatment tool from the channel 34. The user pulls out the endoscope 10 from the subject for examination, and terminates the examination or treatment. The user removes the elevator attachment 90 from the endoscope 10 according to the procedure described with reference to FIG. 36 to FIG. 39 and discards it. The user removes and discards the balloon 98. It is noted that the elevator attachment 90 and the balloon 98 may be removed in any order.

The user performs reprocessing in preparation for a next use on the endoscope 10 from which the elevator attachment 90 and the balloon 98 have been removed. Since the elevator 80 is removed, the user can easily perform a cleaning work.

The balloon 98 may be supplied by being enclosed together with the elevator attachment 90. The user can put out both of the elevator attachment 90 and the balloon 98 to be used for a single case of an ultrasound endoscopy at a time.

As illustrated in FIG. 3, FIG. 5 and FIG. 12, the engagement concave part 57 is a groove linearly provided from the second inner wall 562 of the elevator recess 56 to the outer surface of the distal end frame 52. Likely, the holding groove 58 is linearly provided from the first inner wall 561 of the elevator recess 56 to the outer surface of the distal end frame 52. Thus, the user can easily brush, for example, the inner surface of the engagement concave part 57 and the holding groove 58 when cleaning the endoscope after removal of the elevator attachment 90.

The engagement concave part 57 may be a groove having such a length from the second inner wall 562 as to engage with the engagement protrusion 727, not reaching the periphery of the distal end frame 52. Even such a groove enables cleaning of the inner surface of the engagement concave part 57 using a cleaning brush or the like with a suitable size.

The holding groove 58 may be a groove having such a length from the first inner wall 561 as to permit insertion of the first projection 451 or the like, not reaching the periphery of the distal end frame 52. Even such a groove enables cleaning of the inner surface of the holding groove 58 using a cleaning brush or the like with a suitable size. If the holding groove 58 does not reach the periphery of the distal end frame 52, the holding body 70 does not have the third plate 73.

The holding body 70 needs not be provided with the division slot 728. For example, instead of provision of the division slot 728, by decreasing the wall thickness of the second plate 72 at a corresponding position, the second plate 72 can bend at the vicinity of the stopper protrusion 729 and the engagement protrusion 727.

According to the present embodiment, a forward oblique view type endoscope 10 such as an ultrasound endoscope can be provided that can easily be cleaned by removing the elevator attachment 90 after endoscopy. According to the present embodiment, the elevator attachment 90 is supplied in a state where it is attached to the removable jig 95, which enables easy attachment.

According to the present embodiment, the elevator attachment 90 can easily be removed by using the removable jig 95. The elevator attachment 90 is not disengaged from the removable jig 95, which prevents the elevator attachment 90 from being reused erroneously.

Embodiment 2

The present embodiment relates to the elevator attachment 90 to be removed from the endoscope 10 using a rod-like second jig 92. Contents overlapping those of Embodiment 1 are not repeated.

Figure 40:
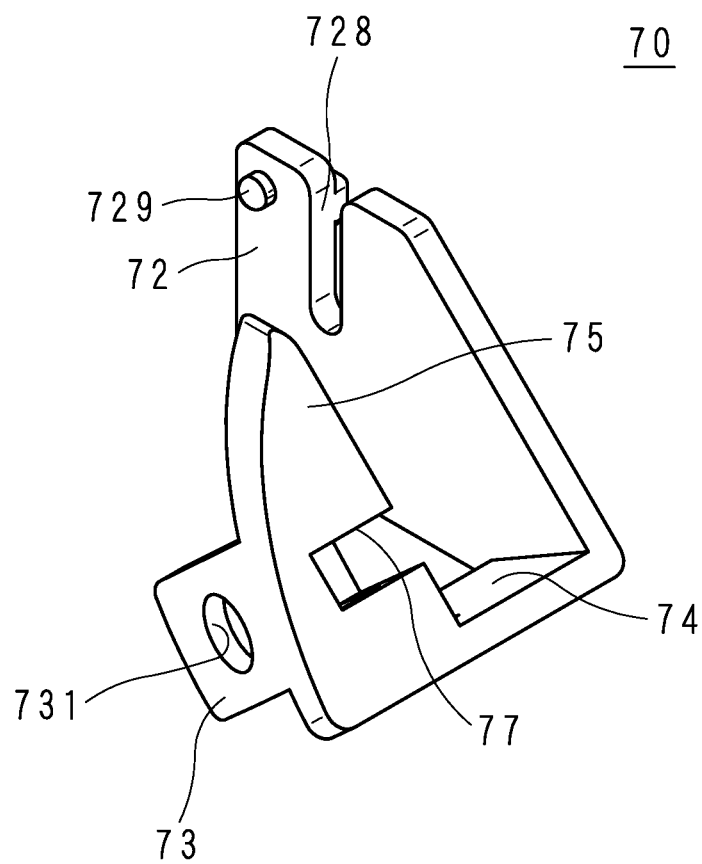
FIG. 40 is a perspective view of a holding body according to Embodiment 2.

FIG. 40 is a perspective view of a holding body 70 according to Embodiment 2. The holding body 70 according to the present embodiment has a jig hole 731 penetrating the third plate 73.

FIG. 41 illustrates a method of removing the elevator attachment 90 according to Embodiment 2 from the endoscope 10. The second jig 92 according to the present embodiment is a stepped round-bar. The small-diameter section of the second jig 92 can be inserted into the jig hole 731. The second jig 92 may be formed with the first jig 91 as one piece as in Embodiment 1 or may be separate from the first jig 91.

The user inserts the second jig 92 through the jig hole 731 to press the engaging pawl 711, elastically deforming the first plate 71 toward the second plate 72, which separates the engaging pawl 711 from the inner wall pawl 581. The user moves the second jig 92 to the right in FIG. 41 in this state to thereby remove the elevator attachment 90 from the endoscope 10. The user can pull out the second jig 92 from the elevator attachment 90.

According to the present embodiment, the elevator attachment 90 can be removed from the second jig 92 without being damaged and thus can be reused after cleaning and sterilization.

Embodiment 3

The present embodiment relates to an endoscope 10 not provided with the ultrasound probe 61. Contents overlapping those of Embodiment 1 are not repeated.

Figure 42:
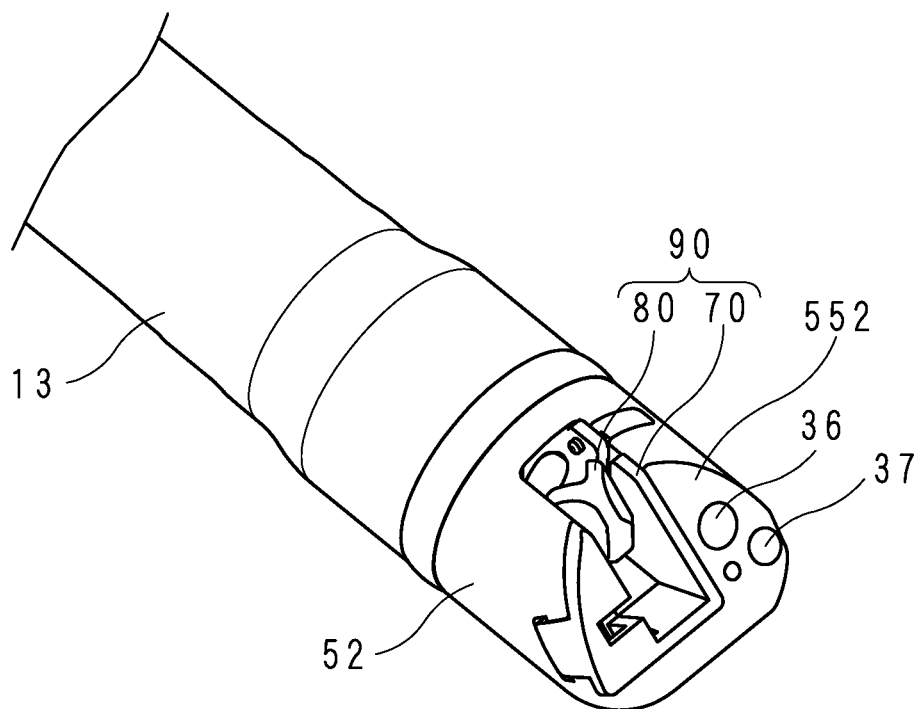
FIG. 42 is a perspective view of the distal end of an insertion part according to Embodiment 3.

FIG. 42 is a perspective view of the distal end of the insertion part 30 according to Embodiment 3. The endoscope 10 according to the present embodiment, which is not provided with the ultrasound probe 61, is a normal forward oblique view type endoscope. The extension of the distal end rigidity is short in comparison with the ultrasound endoscope according to Embodiment 1, which can reduce a load on the body of a patient.

The technical features (elements) described in the embodiments can be combined with each other and can form a new technical feature by the combination.

It should be considered that the embodiments disclosed this time are illustrative in all aspects and are not limitative. The scope of the present invention is indicated not by the meaning described above but by the claims, and all changes that fall within the meaning equivalent to the claims and the scope are to be embraced.

It is to be noted that, as used herein and in the appended claims, the singular forms "a", "an", and "the" include plural referents unless the context clearly dictates otherwise.

DESCRIPTION OF REFERENCE NUMERALS

10 endoscope
12 flexible section
13 bending section
16 first connector
17 second connector
18 first tube
19 second tube
20 operation part
21 elevator operation lever
22 channel inlet
23 bending knob
25 water supply button
30 insertion part
34 channel
36 observation window
37 illumination window
41 first abutting portion
42 second abutting portion
43 elastic plate
431 first retention projection
442 second retention projection
443 third retention projection
451 first projection
452 second projection
454 fourth retention projection
52 distal end frame
53 balloon fixing groove
54 lever
55 inclined surface
551 first inclined surface
552 second inclined surface
56 elevator recess
561 first inner wall
562 second inner wall
57 engagement concave part
58 holding groove
581 inner wall pawl
582 stepped portion
61 ultrasound probe
63 ultrasound wave transmitting and receiving surface
64 balloon water supply and drain groove
70 holding body
71 first plate
711 engaging pawl
72 second plate
721 first side
722 second side
723 third side
724 fourth side
725 fifth side
727 engagement protrusion
728 division slot
729 stopper protrusion
73 third plate
731 jig hole
74 connection part
75 inclined surface plate
76 elevator attachment hole
77 cutaway portion
80 elevator
81 lever connection part
82 elevator shaft
83 elevating part
831 first elevating part
832 second elevating part
833 circular part
84 recess
85 shaft stopper
90 elevator attachment 91 first jig
92 second jig
95 removable jig
96 holding part
98 balloon
99 sterile package

What is claimed:

1. An elevator attachment configured to be attachable to and detachable from an endoscope, the endoscope including:
   an inclined surface inclined relative to a longitudinal direction of an insertion part,
   an elevator recess having a first inner wall and a second inner wall that faces the first inner wall and having an opening that opens toward the inclined surface, and
   a lever pivotally provided inside the elevator recess,
   the elevator attachment comprising:
      a holding body including an inclined surface plate configured to cover a part of the inclined surface of the endoscope, a first plate extending from an edge of the inclined surface plate and configured to be located along the first inner wall of the endoscope, and a second plate configured to abut against the second inner wall; and
      an elevator pivotally supported between the first plate and the second plate and including a lever connection part configured to be connected to the lever of the endoscope, wherein
   the holding body includes a connection part connecting the inclined surface plate and the second plate,
   the second plate has a stopper protrusion protruding toward a side of the first plate, and
   the elevator is configured to be restricted in pivoting by the stopper protrusion and the connection part.

2. The elevator attachment according to claim 1, wherein the second plate includes an engagement protrusion configured to be engaged with an engagement concave part provided on the second inner wall.

3. The elevator attachment according to claim 1, wherein the inclined surface plate has a U-shaped cutaway portion opened toward an edge that the first plate extends to.

4. The elevator attachment according to claim 1, wherein the holding body includes a third plate extending from an edge of the inclined surface plate and facing the first plate.

5. An endoscope, comprising:
   an inclined surface inclined relative to a longitudinal direction of an insertion part;
   an elevator recess having a first inner wall and a second inner wall that faces the first inner wall and being opened toward the inclined surface;
   a lever supported by the second inner wall and pivoting inside the elevator recess;
   an inner wall pawl provided on a side of the first inner wall and to be engaged with an engaging pawl provided in an elevator attachment comprising an elevator to be engaged with the lever; and
   the elevator attachment according to claim 1.

6. The endoscope according to claim 5, wherein the inner wall pawl is provided on a side surface of a holding groove that penetrates the first inner wall and is opened toward the inclined surface.

7. The endoscope according to claim 5, wherein the second inner wall is provided with an engagement concave part to be engaged with the engagement protrusion provided in the elevator attachment.

8. The endoscope according to claim 7, wherein the engagement concave part is a groove.

9. The endoscope according to claim 5, wherein an ultrasound probe is provided more toward a distal end side than the elevator recess.

10. The endoscope according to claim 5, further comprising a forward-oblique-view-typed observation optical system.

11. An elevator attachment configured to be attachable to and detachable from an endoscope, the endoscope including:
   an inclined surface inclined relative to a longitudinal direction of an insertion part,
   an elevator recess having a first inner wall and a second inner wall that faces the first inner wall and having an opening that opens toward the inclined surface, and
   a lever pivotally provided inside the elevator recess,
   the elevator attachment comprising:
      a holding body including an inclined surface plate configured to cover a part of the inclined surface of the endoscope, a first plate extending from an edge of the inclined surface plate and configured to be located along the first inner wall of the endoscope, and a second plate configured to abut against the second inner wall; and
      an elevator pivotally supported between the first plate and the second plate and including a lever connection part configured to be connected to the lever of the endoscope,
   wherein the first plate has an engaging pawl configured to be engaged with an inner wall pawl provided on a side of the first inner wall.

12. The elevator attachment according to claim 11, wherein the engaging pawl protrudes from a main surface of the first plate not facing the second plate and from both side surfaces of the first plate.

* * * * *